US010913930B2

(12) United States Patent
Bhattacharyya et al.

(10) Patent No.: US 10,913,930 B2
(45) Date of Patent: *Feb. 9, 2021

(54) TISSUE PROCESSING APPARATUS AND METHOD FOR INFUSING BIOACTIVE AGENTS INTO TISSUE

(71) Applicant: Warsaw Orthopedic, Inc., Warsaw, IN (US)

(72) Inventors: Subhabrata Bhattacharyya, Metuchen, NJ (US); David R. Kaes, Toms River, NJ (US); Daniel A. Shimko, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/232,275

(22) Filed: Aug. 9, 2016

(65) Prior Publication Data

US 2018/0044638 A1 Feb. 15, 2018

(51) Int. Cl.

| C12N 5/077 | (2010.01) |
| A61F 2/46 | (2006.01) |
| G01N 1/31 | (2006.01) |
| A61L 27/54 | (2006.01) |

(52) U.S. Cl.
CPC .......... *C12N 5/0654* (2013.01); *A61F 2/4644* (2013.01); *A61F 2250/0067* (2013.01); *A61L 27/54* (2013.01); *A61L 2430/02* (2013.01); *A61L 2430/40* (2013.01); *G01N 1/31* (2013.01); *G01N 2001/315* (2013.01)

(58) Field of Classification Search
CPC ........................... G01N 35/0092; A61B 10/00
See application file for complete search history.

(56) References Cited

U.S. PATENT DOCUMENTS

| 5,006,109 | A | * | 4/1991 | Douglas | ............... | A61M 13/003 |
| | | | | | | 600/560 |
| 6,630,153 | B2 | | 10/2003 | Long et al. | | |
| 7,435,383 | B2 | | 10/2008 | Tseung et al. | | |
| 7,642,093 | B2 | | 1/2010 | Tseung et al. | | |
| 7,794,411 | B2 | | 9/2010 | Ritchart et al. | | |
| 7,901,941 | B2 | | 3/2011 | Tseung et al. | | |
| 7,918,803 | B2 | | 4/2011 | Ritchart et al. | | |
| 7,922,688 | B2 | | 4/2011 | Bodduluri et al. | | |
| 7,981,050 | B2 | | 7/2011 | Ritchart et al. | | |
| 7,996,968 | B2 | | 8/2011 | Genova et al. | | |
| 8,020,263 | B2 | | 9/2011 | Genova et al. | | |
| 8,034,292 | B2 | | 10/2011 | Allen et al. | | |
| 8,039,433 | B2 | | 10/2011 | McKay | | |

(Continued)

*Primary Examiner* — William H. Beisner
(74) *Attorney, Agent, or Firm* — Sorell, Lenna & Schmidt, LLP

(57) ABSTRACT

A tissue treatment apparatus and method for treating bone tissue has a controller, an enclosure, a reagent supply system, a draining configuration, and a gas relief valve is controlled by the controller. A bioactive agent may be applied through the reagent supply system. Optionally provided is a gas evacuation assembly, a gas supply unit, a thermal unit for heating or cooling reagents or gases, a sonication unit, any or each operated by the controller. The method provides for programming controller to effect a treatment procedure. In an embodiment of the present application the treatment procedure effects demineralization of the bone material.

5 Claims, 14 Drawing Sheets

(56) References Cited

U.S. PATENT DOCUMENTS

| | | |
|---|---|---|
| 8,114,615 B2 | 2/2012 | Gough et al. |
| 8,162,252 B2 | 4/2012 | Cittadino et al. |
| 8,188,038 B2 | 5/2012 | McKay |
| 8,249,326 B2 | 8/2012 | Macaulay et al. |
| 8,275,182 B2 | 9/2012 | Badiei et al. |
| 8,287,465 B2 | 10/2012 | Hardin et al. |
| 8,347,890 B2 | 1/2013 | Li |
| 8,412,739 B2 | 4/2013 | Engelko et al. |
| 8,428,887 B2 | 4/2013 | Gholap et al. |
| 8,492,140 B2 | 7/2013 | Smith et al. |
| 8,496,198 B2 | 7/2013 | Cittadino et al. |
| 8,559,693 B2 | 10/2013 | Macaulay et al. |
| 8,585,987 B2 | 11/2013 | Tseung et al. |
| 8,594,401 B2 | 11/2013 | Mori et al. |
| 8,597,899 B2 | 12/2013 | Gough et al. |
| 8,597,936 B2 | 12/2013 | Merz |
| 8,734,735 B2 | 5/2014 | Williamson et al. |
| 8,788,214 B2 | 7/2014 | Klein |
| 8,857,439 B2 | 10/2014 | Hedge et al. |
| 8,882,020 B2 | 11/2014 | Cittadino et al. |
| 8,986,214 B2 | 3/2015 | Shachar et al. |
| 9,003,696 B2 | 4/2015 | Deppermann et al. |
| 9,109,198 B2 | 8/2015 | Khan et al. |
| 9,230,063 B2 | 1/2016 | Bhargava et al. |
| 9,308,296 B2 | 4/2016 | Bhattacharyya et al. |
| 9,504,435 B2 | 11/2016 | Bernhardt et al. |
| 9,547,058 B2 | 1/2017 | Miyazaki et al. |
| 9,779,283 B2 | 10/2017 | Bhargava et al. |
| 2004/0091459 A1 | 5/2004 | Nimni |
| 2005/0251268 A1 | 11/2005 | Truncale |
| 2006/0148063 A1* | 7/2006 | Fauzzi ............... G01N 1/31 435/286.4 |
| 2006/0167377 A1 | 7/2006 | Ritchart et al. |
| 2006/0188954 A1 | 8/2006 | Baunoch et al. |
| 2007/0224699 A1 | 9/2007 | Gates |
| 2009/0234673 A1 | 9/2009 | Li et al. |
| 2010/0087946 A1 | 4/2010 | Postel et al. |
| 2010/0098746 A1 | 4/2010 | King |
| 2010/0129859 A1 | 5/2010 | Allen et al. |
| 2010/0256643 A1 | 10/2010 | Glielmo et al. |
| 2011/0295267 A1 | 12/2011 | Tanner et al. |
| 2012/0028298 A1 | 2/2012 | Takayama et al. |
| 2012/0052063 A1 | 3/2012 | Bhargava et al. |
| 2012/0310366 A1 | 12/2012 | Li et al. |
| 2013/0092176 A1 | 4/2013 | Li |
| 2013/0137136 A1 | 5/2013 | Cobb et al. |
| 2013/0182922 A1 | 7/2013 | Kil |
| 2013/0292869 A1 | 11/2013 | McDonald et al. |
| 2013/0338479 A1 | 12/2013 | Pogue et al. |
| 2015/0297793 A1 | 10/2015 | McKay |
| 2015/0306276 A1 | 10/2015 | Shimp |

\* cited by examiner

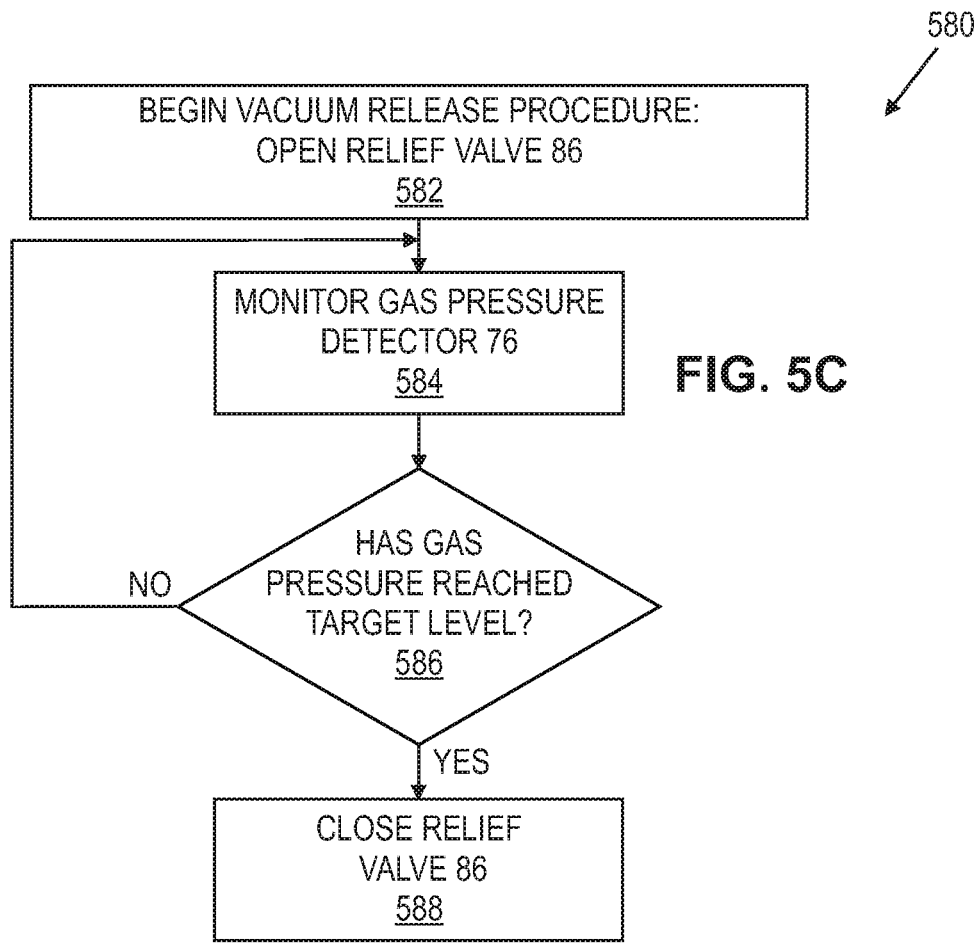

TISSUE PROCESSING APPARATUS AND METHOD FOR INFUSING BIOACTIVE AGENTS INTO TISSUE

BACKGROUND

The rapid and effective repair of bone defects caused by injury, disease, wounds, or surgery is a goal of orthopedic surgery. Toward this end, a number of compositions and materials have been used or proposed for use in the repair of bone defects. The biological, physical, and mechanical properties of the compositions and materials are among the major factors influencing their suitability and performance in various orthopedic applications.

Autologous bone ("ACB"), also known as autograft or autogenous bone, is considered the gold standard for bone grafts. Autograft bone is osteoinductive and nonimmunogenic, and, by definition, has all of the appropriate structural and functional characteristics appropriate for the particular recipient. Unfortunately, autograft bone is only available in a limited number of circumstances. Some individuals lack autograft bone of appropriate dimensions and quality for transplantation, and donor site pain and morbidity can pose serious problems for patients and their physicians.

Much effort has been invested in the identification or development of alternative bone graft materials. Demineralized bone matrix ("DBM") implants have been reported to be particularly useful. Demineralized bone matrix is typically derived from cadavers. The bone is removed aseptically and/or treated to kill any infectious agents. The bone is then optionally particulated by milling or grinding. The bone is then treated to remove fats and to extract the mineral components for example, by soaking the bone in an acidic solution.

The process of preparing tissues, such as DBM for implantation purpose is laborious and slow. The process as presently executed requires a technician to manually treat each tissue sample in a manner that prevents contamination of the tissue. Hence, treating tissue samples from multiple donors requires that cumbersome isolators be used in a laboratory room to prevent cross contamination between samples. Furthermore, variations in the processing, which are inherent due to the manual nature of the processing, results in final product variations that reduce the quality of the resultant product. Since the processing is manual and repetitive, mistakes are made which require rework and waste of sample material.

The processing of tissues also requires sufficient area for a technician to work on each sample, with the area requirements being increased if isolators are required to prevent cross contamination of samples. As a result, as demand for treated tissue increases, a ramp up of production will require large areas for multiple technicians to prepare the tissue samples using existing manual equipment and methods.

In view of the difficulties posed in processing tissue samples from multiple donors, devices and methods are needed to expedite the processing and to improve the quality of process such that samples are consistently prepared according to governmental requirements and quality control. A need therefore exists to process tissue from biologic sources, or example a bone tissue, for purposes of using in materials to be implanted in human or animal recipients and pharmaceutical preparations.

SUMMARY

A processing system suitable for improving the processing of tissue samples (e.g., bone tissue, soft tissue) to produce treated tissue, such as for example, demineralized bone matrix (DBM) is provided. In certain embodiments, a tissue treatment apparatus and method for effecting treatment of biologic tissue sample (e.g., bone tissue, soft tissue) in accordance with programmed procedures. The tissue treatment apparatus has an enclosure for holding a tissue sample in an air tight reaction chamber. A reagent supply system is connected to the enclosure to supply one or more reagents into the reaction chamber. In some aspects, the one or more reagents can be a bioactive agent(s). A controller controls the reagent supply system to effect feeding and dispensing of reagents. The enclosure has a draining configuration under control of the controller. The enclosure also has a gas relief valve controlled by the controller for releasing gases from the enclosure. Optionally provided is a gas evacuation assembly for pumping gas out of the reaction chamber under the control of the controller. Further optionally provided is a gas supply unit under control of the controller. The gas supply unit introduces at least one gas into the reaction chamber. Still further optionally provided is a thermal unit for heating or cooling reagents or gases applied to the tissue sample. The thermal unit is also controlled by the controller. Another optionally provided feature is a sonication unit controlled by the controller to effect sonication of contents of the reaction chamber. The controller is programmed to effect control of the tissue treatment apparatus in accordance with a treatment procedure. In an embodiment of the present application, the tissue sample is bone material and the treatment procedure effects demineralization of the bone material.

In an embodiment of the present application a tissue processing apparatus for processing a biologic tissue sample, for example a bone tissue, is provided and comprises a controller, an enclosure defining a reaction chamber for accepting the tissue sample, and a reagent supply system configured to receive at least one reagent and to dispense the at least one reagent into the reaction chamber in response to the controller. In various embodiments, the at least one reagent is a bioactive reagent, for example a growth factor, a bone morphogenetic protein, an analgesic, an antibiotic, an anti-inflammatory, a cytokine, a chemotherapeutic or a mixture thereof. The tissue processing apparatus has a gas evacuation assembly communicated to the reaction chamber and is configured to pump gas from the reaction chamber in response to the controller. A draining assembly is communicated to the reaction chamber and configured to drain fluid from the reaction chamber in response to the controller. The tissue processing apparatus has a signal transmission system functionally interconnecting the controller with the reagent supply system, the gas evacuation assembly, and the draining assembly.

Another embodiment of the present application includes the above embodiment further comprising a fluid level detector disposed to detect a fluid level in the reaction chamber and communicate the fluid level to the controller via the signal transmission system.

Yet another embodiment of the present application includes any of the above embodiments further comprising a gas pressure detector disposed to detect a gas pressure in the reaction chamber and communicate the gas pressure to the controller via the signal transmission system.

Still another embodiment of the present application includes any of the above embodiments further comprising a carbon dioxide sensor communicated to the reaction chamber to detect a carbon dioxide level in the reaction chamber and communicate the carbon dioxide level to the controller via the signal transmission system.

A further embodiment of the present application includes any of the above embodiments further comprising a gas supply unit communicated to the reaction chamber and configured to receive at least one gas and dispense the at least one gas into the reaction chamber in response to the controller. The gas supply unit is functionally interconnected with the controller via the signal transmission system.

A still further embodiment of the present application includes any of the above embodiments further comprising a thermal assembly configured to effect at least one of heating or cooling of at least one of the at least one reagent, the at least one gas, or contents of the reaction chamber. The thermal assembly is controlled by the controller.

In yet a further embodiment of the present application includes any of the above embodiments further comprising a sonication unit configured to effect sonication of contents of the reaction chamber, wherein the sonication unit is controlled by the controller.

The present application provides an embodiment of a method for treating a biologic tissue sample, for example, a bone tissue sample. The method comprises providing a controller, an enclosure defining a reaction chamber for accepting the tissue sample, and a reagent supply system configured to receive at least one reagent and to dispense the at least one reagent into the reaction chamber in response to the controller. In various embodiments, the reagent supply system is configured to receive and dispense at least a bioactive agent in response to the controller. The method also comprises providing a gas evacuation assembly communicated to the reaction chamber and configured to pump gas from the reaction chamber in response to the controller, and a draining assembly communicated to the reaction chamber and configured to drain fluid from the reaction chamber in response to the controller. The method further comprises a signal transmission system functionally interconnecting the controller with the reagent supply system, the gas evacuation assembly, and the draining assembly. In accordance with the method, the controller is loaded with a treatment procedure programming for affecting a treatment procedure. The method also comprises loading the reagent supply system with a first reagent, disposing the biologic tissue sample in the reaction chamber. Following loading the treatment procedure programming and the reagent, the controller is activated to effect application of the first reagent to the biologic tissue sample by the controller activating the reagent supply system to dispense a predetermined amount of the first reagent into the reaction chamber in accordance with the treatment procedure programming, and draining of the first reagent from the reaction chamber by the controller activating the draining assembly to drain the first reagent from the reaction chamber, after a predetermined time period has passed since the application of the first reagent to the biologic tissue sample, in accordance with the treatment procedure programming.

Another embodiment of a method of the present application includes the above embodiment further comprising effecting evacuation of the reaction chamber to a predetermined pressure level by the controller activating the gas evacuation assembly to evacuate gas from the reaction chamber during the application of the first reagent to the biologic tissue sample in accordance with the treatment procedure programming.

Yet another embodiment of a method of the present application includes any of the above embodiments further comprising providing a carbon dioxide sensor communicated to the reaction chamber to detect a carbon dioxide level in the reaction chamber and communicate the carbon dioxide level to the controller via the signal transmission system, and maintaining a $CO_2$ level in the reaction chamber below a predetermined $CO_2$ level during the application of the first reagent to the biologic tissue sample by the controller monitoring the $CO_2$ level in the reaction chamber, and activating the gas evacuation assembly in response to the $CO_2$ level rising above the predetermined $CO_2$ level, to bring the $CO_2$ level to or below the predetermined $CO_2$ level in accordance with the treatment procedure programming. In such an embodiment, the method optionally provides that the biologic tissue sample is bone material and the first reagent is an acid suitable for demineralizing the bone material.

Still yet another embodiment of a method of the present application includes any of the above embodiments further comprising loading the reagent supply system with a second reagent, effecting application of the second reagent to the biologic tissue sample by the controller activating the reagent supply system to dispense a predetermined amount of the second reagent into the reaction chamber in accordance with the treatment procedure programming, and effecting draining of the second reagent from the reaction chamber by the controller activating the draining assembly to drain the second reagent from the reaction chamber, after a predetermined time period has passed since the application of the second reagent to the bone tissue sample in accordance with the treatment procedure programming. In an aspect of the present application, the second reagent is water.

A further embodiment of a method of the present application includes any of the above embodiments further comprising loading the reagent supply system with a third reagent, effecting application of the third reagent to the biologic tissue sample by the controller activating the reagent supply system to dispense a predetermined amount of the into the reaction chamber in accordance with the treatment procedure programming, and effecting draining of the third reagent from the reaction chamber by the controller activating the draining assembly to drain the third reagent from the reaction chamber, after a predetermined time period has passed since the application of the third reagent to the biologic tissue sample, in accordance with the treatment procedure programming. In an application in accordance with the present application the third reagent or any reagent loaded can be an alcohol suitable for delipidizing bone material.

A still further embodiment of a method of the present application includes any of the above embodiments further comprising loading the reagent supply system with a fourth reagent, effecting application of the fourth reagent to the biologic tissue sample by the controller activating the reagent supply system to dispense a predetermined amount of the fourth reagent into the reaction chamber in accordance with the treatment procedure programming, and effecting draining of the fourth reagent from the reaction chamber by the controller activating the draining assembly to drain the fourth reagent from the reaction chamber, after a predetermined time period has passed since the application of the fourth reagent to the biologic tissue sample, in accordance with the treatment procedure programming. In accordance with a feature of the present application the fourth reagent optionally is a chemical chaperone suitable for at least partially reversing or preventing denaturation of proteins of bone material. In still another embodiment of a method of the present application the fourth reagent or any reagent loaded can be glycerol.

A further embodiment of a method of the present application includes any of the above embodiments further comprising loading the reagent supply system with a bioactive agent, effecting application of the bioactive agent to the biologic tissue sample by the controller activating the reagent supply system to dispense a predetermined amount of the bioactive agent into the reaction chamber in accordance with the treatment procedure programming, and effecting draining of the bioactive agent from the reaction chamber by the controller activating the draining assembly to drain the bioactive agent from the reaction chamber, after a predetermined time period has passed since the application of the bioactive agent to the biologic tissue sample, in accordance with the treatment procedure programming. In some embodiments, the bioactive agent can be applied in lieu of or after the application of the first reagent. In other embodiments, the bioactive agent can be applied in lieu of or after the application of the second reagent. In certain embodiments, the bioactive agent can be applied in lieu of or after the application of the third reagent, the fourth reagent and/or the nth reagent, as described in more detail in this application.

Another embodiment of a method of the present application includes any of the above embodiments further comprising providing a thermal assembly configured to effect at least one of heating or cooling of at least one of the first reagent or contents of the reaction chamber, wherein the thermal assembly is controlled by the controller, and effecting heating of the first reagent to a predetermine temperature by the thermal assembly in response to control thereof by the controller such that the first reagent is at the predetermined temperature when in contact with the tissue sample in the enclosure in accordance with the treatment procedure programming. In one embodiment, the biologic tissue sample is bone material, the first reagent is an acid suitable for demineralizing the bone material, and the predetermined temperature is in the range of 40 degrees Celsius to 120 degrees Celsius.

Yet another embodiment of a method of the present application includes any of the above embodiments further comprising providing a gas supply unit communicated to the reaction chamber and configured to receive at least one gas and dispense the at least one gas into the reaction chamber in response to the controller, the gas supply unit being functionally interconnected with the controller via the signal transmission system, providing a thermal assembly configured to effect at least one of heating or cooling of at least one of the first reagent or contents of the reaction chamber, wherein the thermal assembly is controlled by the controller. The embodiment further provides effecting evacuation of the enclosure by the gas evacuation assembly in response to control thereof by the controller in accordance with the treatment procedure programming, effecting charging of the enclosure with the at least one gas by operation of the gas supply unit in response to control thereof by the controller in accordance with the treatment procedure programming, and effecting heating of the at least one gas to a predetermine temperature by the thermal assembly in response to control thereof by the controller, such that the at least one gas is at the predetermined temperature when in contact with the tissue sample in the enclosure in accordance with the treatment procedure programming. The method also optionally includes the biologic tissue sample being bone material, the at least one gas being not oxygen, and the predetermined temperature being in the range of from about −20, −10, −5, −2, −1, 0, 5, 10, 15, 20, 25, 30, 35, or 40 degrees Celsius to 120 degrees Celsius to allow in some embodiments the reaction to go to completion.

Still another embodiment of a method of the present application includes any of the above embodiments further comprising the at least one gas being supercritical carbon dioxide and the controller being programmed to adjust pressure of the supercritical carbon dioxide to adjust properties thereof between gas properties and liquid properties to vary solvent action thereof.

Still yet another embodiment of a method of the present application includes any of the above embodiments further comprising providing a sonication unit configured to effect sonication of contents of the reaction chamber, wherein the sonication unit is controlled by the controller, and effecting sonication of the first or any reagent by the sonication unit in response to control thereof by the controller such that the reagent is sonicated at a predetermined level when in contact with the tissue sample in the enclosure in accordance with the treatment procedure programming. The embodiment further optionally provides that the biologic tissue sample is bone material, and the first reagent is an acid suitable for demineralizing the bone material.

The above and other objects, features and advantages of the present application will become apparent from the following description read in conjunction with the accompanying drawings, in which like reference numerals designate the same elements. The present application is considered to include all functional combinations of the above described features and is not limited to the particular structural embodiments shown in the figures as examples. The scope and spirit of the present application are considered to include modifications as may be made by those skilled in the art having the benefit of the present disclosure which substitute, for elements presented in the claims, devices or structures upon which the claim language reads or which are equivalent thereto, and which produce substantially the same results associated with those corresponding examples identified in this disclosure for purposes of the operation of this application. Furthermore, operations in accordance with methods of the description and claims are not intended to be required in any particular order unless necessitated by prerequisites included in the operations. Additionally, the scope and spirit of the present application is intended to be defined by the scope of the claim language itself and equivalents thereto without incorporation of structural or functional limitations discussed in the specification which are not referred to in the claim language itself. Accordingly, the detailed description is intended as illustrative in nature and not limiting the scope and spirit of the present application.

BRIEF DESCRIPTION OF THE DRAWINGS

FIG. 5c is a flow chart of an embodiment of an operating procedure for releasing a vacuum or pressurization according to an aspect of the present application;

FIG. 5d is a flow chart of another embodiment of an operating procedure for releasing a vacuum or pressurization according to an aspect of the present application;

DETAILED DESCRIPTION

Definitions

Figure 1:
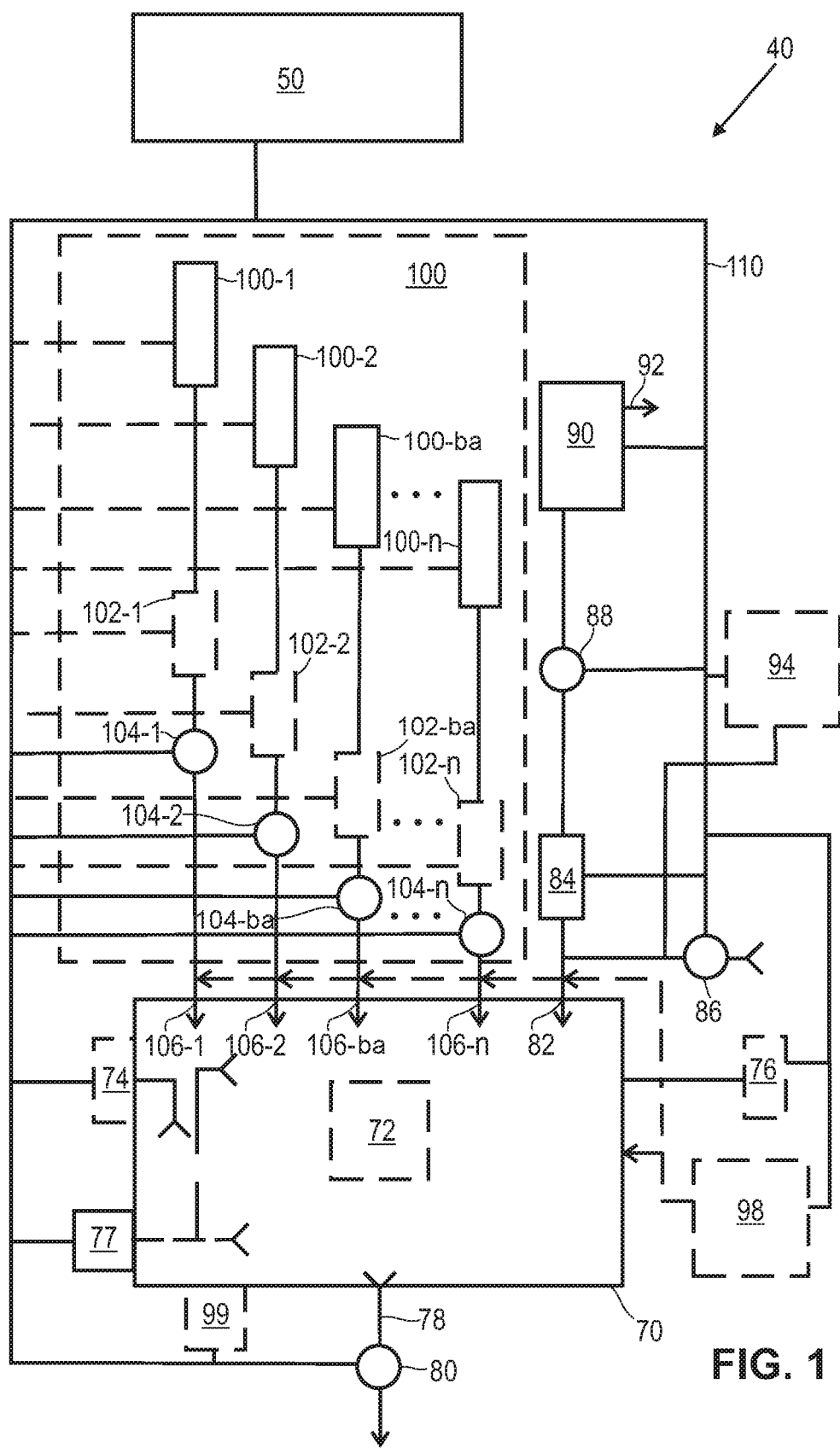
FIG. 1 is a block diagram of an embodiment of a tissue processing apparatus according to an aspect of the present application.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Bioactive agent or bioactive compound is used herein to refer to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, antibodies, interleukins, growth factors, antibiotics, anti-inflammatory agents, analgesics, vaccines, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, imaging agents and any combinations thereof. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. Bioactive agents that can be introduced into the system and added to the bone tissue also include, for example, vitamins, anabolic agents, catabolic agents, pH altering substances, ionic or pH buffers, oxysterols or modified oxysterols (e.g., OXY133, OXY149, etc.), nitrous oxide and/or oxygen emitters/scavengers or a combination thereof. A more complete listing of bioactive agents and specific drugs suitable for use in the present application may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", edited by Susan Budavari et al., CRC Press, 1996; and the United States Pharmacopeia-25/National Formulary-20, published by the United States Pharmacopeia Convention, Inc., Rockville Md., 2001, each of which is incorporated herein by reference.

These bioactive agents, when introduced into the bone tissue, can interact with Eukaryotic and/or Prokaryotic cells to exert their bioactivity (for example, killing or inhibiting Prokaryotic cells such as bacteria or enhancing bone specific Eukaryotic cell activity, such as for example, osteoblast, osteoclasts, osteocytes, mesenchymal stem cells, etc.).

Biocompatible, as used herein, is intended to describe materials that, upon administration in vivo, do not induce undesirable long-term effects.

Biodegradable, as used herein, includes that all or parts of the implant will degrade over time by the action of enzymes, by hydrolytic action and/or by other similar mechanisms in the human body. In various embodiments, "biodegradable" includes that the implant can break down or degrade within the body to non-toxic components after or while a therapeutic agent has been or is being released. By "bioerodible" it is meant that the carrier and/or implant will erode or degrade over time due, at least in part, to contact with substances found in the surrounding tissue, fluids or by cellular action. By "bioabsorbable" or "bioresorbable" it is meant that the carrier and/or implant will be broken down and absorbed within the human body, for example, by a cell or tissue.

Bone, as used herein, refers to bone that is cortical, cancellous or cortico-cancellous of autogenous, allogenic, xenogenic, or transgenic origin.

Bone graft, as used herein, refers to any implant prepared in accordance with the embodiments described herein and therefore may include expressions such as bone material and bone membrane.

Demineralized, as used herein, refers to any material generated by removing mineral material from tissue, for example, bone tissue. In certain embodiments, the demineralized compositions described herein include preparations containing less than 5% calcium. In some embodiments, the demineralized compositions may comprise less than 1% calcium by weight. In some embodiments, the compositions may comprise less than 5, 4, 3, 2 and/or 1% calcium by weight. Partially demineralized bone is intended to refer to preparations with greater than 5% calcium by weight but containing less than 100% of the original starting amount of calcium. In some embodiments, partially demineralized bone comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% of the original starting amount of calcium.

In some embodiments, demineralized bone has less than 95% of its original mineral content. In some embodiments, demineralized bone less than 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6 and/or 5% of its original content. In some embodiments, "Demineralized" is intended to encompass such expressions as "substantially demineralized," "partially demineralized," "surface demineralized," and "fully demineralized." "Partially demineralized" is intended to encompass "surface demineralized."

In some embodiments, the demineralized bone may be surface demineralized from about 1-99%. In some embodiments, the demineralized bone is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and/or 99% surface demineralized. In various embodiments, the demineralized bone may be surface demineralized from about 15-25%. In some embodiments, the demineralized bone is 15, 16, 17, 18, 19, 20, 21, 22, 23, 24 and/or 25% surface demineralized.

Demineralized bone matrix (DBM), as used herein, refers to any material generated by removing mineral material from bone tissue. In some embodiments, the DBM compositions as used herein include preparations containing less than 5% calcium and, in some embodiments, less than 1% calcium by weight. In some embodiments, the DBM compositions include preparations that contain less than 5, 4, 3, 2 and/or 1% calcium by weight. In other embodiments, the DBM compositions comprise partially demineralized bone (e.g., preparations with greater than 5% calcium by weight but containing less than 100% of the original starting amount of calcium).

Osteoconductive, as used herein, refers to the ability of a substance to serve as a template or substance along which bone may grow.

Osteogenic, as used herein, refers to materials containing living cells capable of differentiation into bone tissue.

Osteoinductive, as used herein, refers to the quality of being able to recruit cells from the host that have the potential to stimulate new bone formation. Any material that can induce the formation of ectopic bone in the soft tissue of an animal is considered osteoinductive. For example, most osteoinductive materials induce bone formation in athymic rats when assayed according to the method of Edwards et al., "Osteoinduction of Human Demineralized Bone: Characterization in a Rat Model," Clinical Orthopaedics & Rel. Res., 357:219-228, December 1998, incorporated herein by reference.

Superficially demineralized, as used herein, refers to bone-derived elements possessing at least about 90 weight percent of their original inorganic mineral content. In some embodiments, superficially demineralized contains at least about 90, 91, 92, 93, 94, 95, 96, 97, 98 and/or 99 weight percent of their original inorganic material. The expression "partially demineralized" as used herein refers to bone-derived elements possessing from about 8 to about 90 weight percent of their original inorganic mineral content. In some embodiments, partially demineralized contains about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and/or 90 weight percent of their original inorganic mineral content. The expression "fully demineralized" as used herein refers to bone containing less than 8% of its original mineral context. In some embodiments, fully demineralized contains about less than 8, 7, 6, 5, 4, 3, 2 and/or 1% of its original mineral content.

"Soft tissue," as used herein, refers to any biological tissue other than bone, including but not limited to tendons, ligaments, fascia, whole joints, dura, skin, pericardia, heart valves, veins, neural tissue, submucosal tissue (e.g. intestinal tissue), and cartilage. The "soft tissue" described herein is typically a collagenous material that is autograft, allograft or xenograft. The soft tissue can be a predetermined length of tendon, a bundle of tendons of the same or different lengths, a predetermined length of ligament, a bundle of ligaments of the same length or different lengths, a segment or segments of pericardium, dermis, fascia, dura, skin, submucosal tissue (e.g., intestinal tissue), cartilage, or a combination thereof. In some embodiments, the source of the soft tissue is a xenograft tendon. In a further embodiment, the critical point dried samples may further be treated, or alternatively be treated, with supercritical carbon dioxide (carbon dioxide above the critical point). Supercritical $CO_2$ may also be useful in viral inactivation. In some embodiments, thus, the bone matrix is placed in a supercritical $CO_2$ chamber and liquid $CO_2$ is introduced, for example, by an air pump. The temperature is raised to 105° C. with corresponding pressure about 485 bar. In alternative embodiments, other temperatures and/or pressures above the critical point of $CO_2$ may be used. The samples are soaked in supercritical $CO_2$ for a certain time and $CO_2$ is released. The resulting bone samples retain surface morphologies, hence surface area, and osteoinductivity after such treatment.

Tissue Material

The tissue material, which can be soft or hard tissue, can be placed in the chamber and then be subject to treatment with one or more reagents in solid, liquid and/or gas form. The addition of the reagents and the draining or evacuation of the reagents in solid, liquid and/or gaseous form is automated and subject to control by a controller. For example, when dealing with hard tissue such as bone, the bone can be demineralized in an automated process. The bone material can be placed in a reaction chamber and then it can be treated with acid where the quantity, time, soak time, generation of reactants, rinse time (e.g., rinse with water, glycerol, etc.), and drainage can be monitored. Conditions such as pressure, temperature, and evacuation from the chamber can be monitored and changed as the reaction proceeds. The apparatus and method provided can also be used to change the porosity of the implant by using pore forming reagents or other reagents. In some embodiments, the depth of demineralization can be controlled by the automated system. In some embodiments, the bone can be in the form of fibers, chips, sheets or the like. The automated tissue processing system of the present application can be used to measure, speed up, slow down and/or maintain the reaction conditions in the reaction chamber as the tissue sample is processed.

Providing Demineralized Bone Material

Following shaving, milling or other technique whereby they are obtained, the bone material is subjected to demineralization in the reaction chamber via the automated process describe under the control of the controller in order to reduce its inorganic content to a very low level, in some embodiments, to not more than about 5% by weight of residual calcium and, in other embodiments, to not more than about 1% by weight residual calcium. Demineralization of the bone material ordinarily results in its contraction to some extent.

Bone used in the methods described herein may be autograft, allograft, or xenograft. In various embodiments, the bone may be cortical bone, cancellous bone, or cortico-cancellous bone. While specific discussion is made herein to demineralized bone matrix, bone matrix treated in accordance with the teachings herein may be non-demineralized, demineralized, partially demineralized, or surface demineralized. The following discussion applies to demineralized, partially demineralized, and surface demineralized bone matrix. In one embodiment, the demineralized bone is sourced from bovine or human bone. In another embodiment, demineralized bone is sourced from human bone. In one embodiment, the demineralized bone is sourced from the patient's own bone (autogenous bone). In another embodiment, the demineralized bone is sourced from a different animal (including a cadaver) of the same species (allograft bone).

Any suitable manner of demineralizing the bone may be used. Demineralization of the bone material can be conducted in accordance with known conventional procedures adapted to use with the present application.

In accordance with a demineralization procedure of the present application until now effected manually by a technician, the bone material useful for the implantable composition of this application can be subjected to an acid demineralization step that is followed by a defatting/disinfecting step. The bone material is immersed in acid over time to effect its demineralization. Acids which can be employed in this step include inorganic acids such as hydrochloric acid and organic acids such as peracetic acid, acetic acid, citric acid, or propionic acid. The depth of demineralization into the bone surface can be controlled by adjusting the treatment time, temperature of the demineralizing solution, concentration of the demineralizing solution, sonication or agitation intensity during treatment, and other applied forces such as vacuum, centrifuge, pressure, and other factors such as known to those skilled in the art. Thus, in various embodiments, the bone material may be fully demineralized, partially demineralized, or surface demineralized.

After acid treatment, the bone is rinsed with sterile water for injection in the chamber, buffered with a buffering agent in the chamber to a final predetermined pH and then finally rinsed with water for injection in the chamber to remove residual amounts of acid and buffering agent or washed with water to remove residual acid and thereby raise the pH. Following demineralization, the bone material is immersed in solution to effect its defatting in the chamber. In various embodiments, a defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. In some embodiments, the concentration range of the defatting solution is from about 60 to 85 weight percent alcohol and, in other embodiments, about 70 weight percent alcohol.

Further in accordance with this application, the DBM material can be used immediately for preparation of the implant composition or it can be stored under aseptic conditions, advantageously in a critical point dried state prior to such preparation. In an embodiment, the bone material can retain some of its original mineral content such that the composition is rendered capable of being imaged utilizing radiographic techniques.

Demineralized Bone Matrix

In various embodiments, this application also provides bone matrix compositions which comprise CPD fibers that are made through the described automated process. DBM includes the collagen matrix of the bone together with acid insoluble proteins including bone morphogenetic proteins (BMPs) and other growth factors. It can be formulated for use as granules, gels, sponge material or putty and can be freeze-dried for storage. Sterilization procedures used to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues.

DBM preparations have been used for many years in orthopedic medicine to promote the formation of bone. For example, DBM has found use in the repair of fractures, in the fusion of vertebrae, in joint replacement surgery, and in treating bone destruction due to underlying disease such as rheumatoid arthritis. DBM is thought to promote bone formation in vivo by osteoconductive and osteoinductive processes. The osteoinductive effect of implanted DBM compositions is thought to result from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

In various embodiments, the DBM provided in the methods and devices described in this application is prepared from elongated bone fibers which have been subjected to critical point drying. The elongated CPD bone fibers employed in this application are generally characterized as having relatively high average length to average width ratios, also known as the aspect ratio. In various embodiments, the aspect ratio of the elongated bone fibers is at least from about 50:1 to about at least about 1000:1. Such elongated bone fibers can be readily obtained by any one of several methods, for example, by milling or shaving the surface of an entire bone or relatively large section of bone.

In other embodiments, the length of the fibers can be at least about 3.5 cm and average width from about 20 mm to about 1 cm. In various embodiments, the average length of the elongated fibers can be from about 3.5 cm to about 6.0 cm and the average width from about 20 mm to about 1 cm. In other embodiments, the elongated fibers can have an average length be from about 4.0 cm to about 6.0 cm and an average width from about 20 mm to about 1 cm.

In yet other embodiments, the diameter or average width of the elongated fibers is, for example, not more than about 1.00 cm, not more than 0.5 cm or not more than about 0.01 cm. In still other embodiments, the diameter or average width of the fibers can be from about 0.01 cm to about 0.4 cm or from about 0.02 cm to about 0.3 cm.

In another embodiment, the aspect ratio of the fibers can be from about 50:1 to about 950:1, from about 50:1 to about 750:1, from about 50:1 to about 500:1, from about 50:1 to about 250:1; or from about 50:1 to about 100:1. Fibers according to this disclosure can advantageously have an aspect ratio from about 50:1 to about 1000:1, from about 50:1 to about 950:1, from about 50:1 to about 750:1, from about 50:1 to about 600:1, from about 50:1 to about 350:1, from about 50:1 to about 200:1, from about 50:1 to about 100:1, or from about 50:1 to about 75:1. To prepare the osteogenic DBM, a quantity of fibers is combined with a biocompatible carrier to provide a demineralized bone matrix.

Providing Dry Bone

After the bone is demineralized, it can be optionally dried using the apparatus of the current application. DBM typically is dried, for example via lyophilization or solvent drying, to store and maintain the DBM in active condition for implantation. Moreover, each of these processes is thought to reduce the overall surface area structure of bone. As may be appreciated, the structural damage of the exterior surface reduces the overall surface area. Physical alterations to the surface and reduction in surface area can affect cell attachment, mobility, proliferation, and differentiation. The surface's affinity for growth factors and release kinetics of growth factors from the surface may also be altered.

Accordingly, in some embodiments, methods for drying bone to store and maintain the bone in active condition for implantation that maintains or increases the surface area of the bone are provided. In one embodiment, the bone matrix is treated using critical point drying (CPD) technique, thereby reducing destruction of the surface of the bone. While specific description is made to critical point drying, it is to be appreciated that, in alternative embodiments, super critical point treatment may be used. In various embodiments utilizing CPD, a percentage of collagen fibrils on the surface of the bone are non-denatured after drying to a residual moisture content of approximately 15% or less. In some embodiments, after drying, the bone matrix has a residual moisture content of approximately 8% or less. In some embodiments, after drying, the bone matrix has a residual moisture content of approximately 6% or less. In some embodiments, after drying, the bone matrix has a residual moisture content of approximately 6% or less. In some embodiments, after drying, the bone matrix has a residual moisture content of approximately 3% or less.

Evaporative drying and freeze drying of specimens can cause deformation and collapse of surface structures, leading to a decrease in surface area. Without wishing to be bound to a particular theory, this deformation and structure is thought to be caused because, as a substance crosses the boundary from liquid to gas, the substance volatilizes such that the volume of the liquid decreases. As this happens, surface tension at the solid-liquid interface pulls against any structures to which the liquid is attached. Delicate surface structures tend to be broken apart by this surface tension. Such damage may be caused by the effects of surface tension on the liquid/gas interface. Critical point drying is a technique that avoids effects of surface tension on the liquid/gas interface by substantially preventing a liquid/gas interface from developing. Critical point or supercritical drying does not cross any phase boundary, instead passing through the supercritical region, where the distinction between gas and liquid ceases to apply. As a result, materials dehydrated using critical point drying are not exposed to damaging surface tension forces. When the critical point of the liquid is reached, it is possible to pass from liquid to gas without abrupt change in state. Critical point drying can be used with bone matrices to phase change from liquid to dry gas without the effects of surface tension. Accordingly, bone dehydrated using critical point drying can retain or increase at least some of the surface structure and therefore the surface area.

In some embodiments, critical point drying is carried out using carbon dioxide. However, other mediums such as Freon, including Freon 13 (chlorotrifluoromethane), may be used. Generally, fluids suitable for supercritical drying include carbon dioxide (critical point 304.25 K at 7.39 MPa or 31.1° C. at 1072 psi or 31.2° C. and 73.8 bar) and Freon (about 300 K at 3.5-4 MPa or 25 to 30° C. at 500-600 psi). Nitrous oxide has similar physical behavior to carbon dioxide, but is a powerful oxidizer in its supercritical state. Supercritical water is also a powerful oxidizer, partly because its critical point occurs at such a high temperature (374° C.) and pressure (3212 psi/647K and 22.064 MPa).

In some embodiments, the bone may be pretreated to remove water prior to critical point drying. Thus, in accordance with one embodiment, bone matrix is dried using carbon dioxide in (or above) its critical point status. After demineralization, bone matrix samples (in water) may be dehydrated to remove residual water content. Such dehydration may be, for example, through a series of graded ethanol solutions (for example, 20%, 50%, 70%, 80%, 90%, 95%, 100% ethanol in deionized water). In some embodiments, penetrating the tissue with a graded series of ethanol solutions or alcohols may be accomplished in an automated fashion. For example, pressure and vacuum could be used to accelerate penetration into the tissue.

In alternative embodiments, other means or procedures for removing water (drying or dehydrating) from the bone may be used. For example, the bone may be washed with other dehydrating liquids such as acetone to remove water, exploiting the complete miscibility of these two fluids. The acetone may then be washed away with high pressure liquid carbon dioxide.

In some embodiments, the dehydrated bone matrix is placed in a chamber within a critical point drying (CPD) apparatus and flushed with liquid $CO_2$ to remove ethanol (or other dehydrating liquid). Flushing with liquid $CO_2$ may be done one or more times. The temperature and/or pressure are then raised to the critical point (the critical point for $CO_2$ is reached at 31.2° C. and 73.8 bar). To perform critical point drying, the temperature and pressure may continue to be raised, for example to 40° C. with corresponding pressure of 85 bar. Thus, in some embodiments, the liquid carbon dioxide is heated until its pressure is at or above the critical point, at which time the pressure can be gradually released, allowing the gas to escape and leaving a dried product.

In certain embodiments, bone fibers processed using CPD have a BET surface area from about 1 to about 5 $m^2/gm$, a value 3 or 4 times greater than lyophilized bone fibers. In other embodiments, DBM fibers processed using CPD have a BET area surface from about 40 to about 100 $m^2/gm$, a value 100 times greater than when DBM fibers are lyophilized.

DBM dried with critical point carbon dioxide has increased biological activity and osteoinductivity when compared to DBM dried by lyophilization.

Bone Powder

In yet a further embodiment, monolithic bone is demineralized and particulated before drying and then placed in the chamber for processing. Accordingly, the bone may be demineralized in monolithic pieces in the chamber as discussed above. The demineralized monolithic pieces may then be milled in a wet condition and critical point dried, for example, using carbon dioxide as a medium.

In yet a further embodiment, monolithic bone is demineralized and dried in the chamber before particulating (if done). Accordingly, the bone may be demineralized in monolithic pieces. The DBM is pressed in a wet condition and then critical point dried, for example, using carbon dioxide as a medium. In alternatives of this embodiment, the demineralized and dried monolithic bone is not particulated and is processed as a monolithic implant.

In various embodiments, the bone may be particulated such as, for example, in bone powder or fiber form. If the bone is demineralized, the bone may be made into a particulate before, during or after demineralization. As previously discussed, in some embodiments, the bone may be monolithic and may not be a particulate. Accordingly, while specific discussion is given to particulate, the methods disclosed herein and the nanoscale textured surfaces disclosed herein may be used with monolithic bones or implants, including, for example, surface demineralized implants or fully demineralized cortical bone implants.

The bone may be milled and ground or otherwise processed into particles of an appropriate size before or after demineralization. The particles may be particulate or fibrous. The terms milling or grinding are not intended to be limited to production of particles of a specific type and may refer to production of particulate or fibrous particles. In certain embodiments, the particle size may be greater than 25 microns, such as ranging from about 25 to about 2000 microns, or from about 25 to about 500 microns or from about 200 to about 1000 microns. In some embodiments, the size of the bone powder particles is less than 100 microns. In some embodiments, the size of the bone powder particles is less than 500 microns.

In some embodiments, the particle size may be 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000, 1005, 1010, 1015, 1020, 1025, 1030, 1035, 1040, 1045, 1050, 1055, 1060, 1065, 1070, 1075, 1080, 1085, 1090, 1095, 1100, 1105, 1110, 1115, 1120, 1125, 1130, 1135, 1140, 1145, 1150, 1155, 1160, 1165, 1170, 1175, 1180, 1185, 1190, 1195, 1200, 1205, 1210, 1215, 1220, 1225, 1230, 1235, 1240, 1245, 1250, 1255, 1260, 1265, 1270, 1275, 1280, 1285, 1290, 1295, 1300, 1305, 1310, 1315, 1320, 1325, 1330, 1335, 1340, 1345, 1350, 1355, 1360, 1365, 1370, 1375, 1380, 1385, 1390, 1395, 1400, 1405, 1410, 1415, 1420, 1425, 1430, 1435, 1440, 1445, 1450, 1455, 1460, 1465, 1470, 1475, 1480, 1485, 1490, 1495, 1500, 1505, 1510, 1515, 1520, 1525, 1530, 1535, 1540, 1545, 1550, 1555, 1560, 1565, 1570, 1575, 1580, 1585, 1590, 1595, 1600, 1605, 1610, 1615, 1620, 1625, 1630, 1635, 1640, 1645, 1650, 1655, 1660, 1665, 1670, 1675, 1680, 1685, 1690, 1695, 1700, 1705, 1710, 1715, 1720, 1725, 1730, 1735, 1740, 1745, 1750, 1755, 1760, 1765, 1770, 1775, 1780, 1785, 1790, 1795, 1800, 1805, 1810, 1815, 1820, 1825, 1830, 1835, 1840, 1845, 1850, 1855, 1860, 1865, 1870, 1875, 1880, 1885, 1890, 1895, 1900, 1905, 1910, 1915, 1920, 1925, 1930, 1935, 1940, 1945, 1950, 1955, 1960, 1965, 1970, 1975, 1980, 1985, 1990, 1995 and/or 2000 microns. After grinding, the bone particles may be sieved to select those particles of a desired size. In certain embodiments, the particles may be sieved though a 25 micron sieve, a 50 micron sieve, a 75 micron sieve, a 100 micron sieve, a 125 micron sieve, a 150 micron sieve, a 175 micron sieve and/or a 200 micron sieve.

In some embodiments, the bone powder comprises DBM and/or mineralized bone. In some embodiments, the size of the bone powder particles is less than 25 microns. In some embodiments, the bone powder particle size is about 1, 2, 3, 4, 5, 6, 7, 8, 9, 10, 11, 12, 13, 14, 15, 16, 17, 18, 19, 20, 21, 22, 23 and/or 24 microns.

Bioactive Agents

For a faster healing, it may be desirable to administer the DBM described in this application with a bioactive agent. In some embodiments, the bioactive agent comprises a small molecule, a protein, a fragment of a protein, a nucleic acid sequence, a cell, or a combination thereof. Small molecule bioactive agents include therapeutic agents, for example antibiotics.

Non-limiting examples of suitable antibiotics include, without limitation nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, omidazole, amifloxacin, cinoxacin, ciprofloxacin, difloxacin, enoxacin, fleroxacin, norfloxacin, ofloxacin, temafloxacin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol or any combination thereof.

In other embodiments, suitable examples of other small molecules include anti-inflammatory compounds both steroidal and non-steroidal and analgesics. Suitable non-limiting examples of steroidal anti-inflammatory compounds are corticosteroids such as hydrocortisone, cortisol, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone. Mixtures of the above steroidal anti-inflammatory compounds can also be used.

Non-limiting examples of non-steroidal anti-inflammatory compounds include nabumetone, celecoxib, etodolac, nimesulide, apasone, gold, oxicams, such as piroxicam, isoxicam, meloxicam, tenoxicam, sudoxicam, and CP-14,304; the salicylates, such as aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; the fenamates, such as mefenamic, meclofenamic, flufenamic, niflumic, and tolfenamic acids; the propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and the pyrazoles, such as phenylbutazone, oxyphenbutazone, feprazone, azapropazone, and trimethazone.

The variety of compounds encompassed by the anti-inflammatory group of agents is well-known to those skilled in the art. For detailed disclosure of the chemical structure, synthesis, side effects, etc. of non-steroidal anti-inflammatory compounds, reference may be made to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974), each incorporated herein by reference. Mixtures of these non-steroidal anti-inflammatory compounds may also be employed, as well as the pharmacologically acceptable salts and esters of these compounds.

In various embodiments, the DBM provided herein may be used with growth factors, extracts, peptide hormones, or other additives to increase the osteoinductive capacity of the DBM or to impart other benefits to the DBM. It will be appreciated that the amount of additive used will vary depending upon the type of additive, the specific activity of the particular additive preparation employed, and the intended use of the composition. The desired amount can be readily determinable by the user.

In some embodiments, a bioactive agent including a therapeutic agent may be disposed on or in the DBM by hand, electrospraying, ionization spraying or impregnating, vibratory dispersion (including sonication), nozzle spraying, compressed-air-assisted spraying, brushing and/or pouring. For example, a growth factor such as rhBMP-2 may be disposed on or in the DBM by the surgeon before the DBM is administered or it may be available from the manufacturer beforehand.

The DBM may comprise at least one growth factor. These growth factors include osteoinductive agents (e.g., agents that cause new bone growth in an area where there was none) and/or osteoconductive agents (e.g., agents that cause in growth of cells into and/or through the DBM). Osteoinductive agents can be polypeptides or polynucleotides compositions. Polynucleotide compositions of the osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenetic Proteins (CDMPs), LIM Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art (See, for example, International Publication No.

WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties. Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenetic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. In certain embodiments of variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within carrier are typically sterile. In a non-limiting method, sterility is readily accomplished for example by filtration through sterile filtration membranes (e.g., 0.2 micron membranes or filters). In one embodiment, the isolated osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2, 4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents include one or more members of the family of Transforming Growth Factor-beta genes ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BC030959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BCO28237 or AAH28237, as well as mature GDF-10 polypeptides or polynucleotides encoding the same.

GDF-11 polynucleotides or polypeptides corresponding to GenBank Accession Numbers AF100907, NP005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same. In another embodiment, isolated osteoinductive agents include Cartilage Derived Morphogenetic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents include, but are not limited to, the following CDMPs and LMPs: CDMP-1 polynucleotides and polypeptides corresponding to GenBank Accession Numbers NM000557, U13660, NP000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents include one or more members of any one of the families of Bone Morphogenetic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenetic Proteins (CDMPs), Lim Mineralization Proteins (LMPs), or Transforming Growth Factor-betas (TGF-betas), TP508 (an angiogenic tissue repair peptide), as well as mixtures or combinations thereof. In another embodiment, the one or more isolated osteoinductive agents useful in the DBM are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and or combination thereof, osteoprotegerin; TGF-beta-1, TGF-beta-2, TGF-beta-3, or any combination thereof; or any combination of one or more members of these groups. In some embodiments, BMP-7 and/or GDF-5 may be used at 1-2 mg/cc of the demineralized bone matrix.

The concentrations of growth factor can be varied based on the desired length or degree of osteogenic effects desired. Similarly, one of skill in the art will understand that the duration of sustained release of the growth factor can be modified by the manipulation of the compositions comprising the sustained release formulation, such as for example, modifying the percent of DBM found within a sustained release formulation, microencapsulation of the formulation within polymers, including polymers having varying degradation times and characteristics, and layering the formulation in varying thicknesses in one or more degradable polymers. These sustained release formulations can therefore be designed to provide customized time release of growth factors that simulate the natural healing process.

In some embodiments, a statin may be used as the growth factor. Statins include, but are not limited to, atorvastatin, simvastatin, pravastatin, cerivastatin, mevastatin (see U.S. Pat. No. 3,883,140, the entire disclosure is herein incorporated by reference), velostatin (also called synvinolin, see U.S. Pat. Nos. 4,448,784 and 4,450,171; these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. Other statins include without limitation, atorvastatin, rivastatin, HMG CoA synthetase inhibitors (e.g., L-659,699 ((E, E)-11-[3'R-(hydroxymethyl)-4'-oxo-2'R-oxetanyl]-3, 5, 7R-trimethyl-2, 4-undecadienoic acid)), and any combinations thereof. In various embodiments, the statin may comprise mixtures of (+) R and (−)-S enantiomers of the statin. In various embodiments, the statin may comprise a 1:1 racemic mixture of the statin.

In various embodiments, the therapeutically effective amount of a bioactive agent that can be placed in the DBM matrix comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 150 mg, 200 mg, 250 mg, 300 mg, 350 mg, 400 mg or 500 mg of antibiotic per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

The bioactive agent may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfate, sodium thiosulfate, thimerosal, methylparaben, polyvinyl alcohol and phenylethyl alcohol; solubility adjusting agents; stabilizers; and/or cohesion modifiers. In some embodiments, the bioactive agent may comprise sterile and/or preservative free material. The sustained release process, for example, may be by a solution-diffusion mechanism or it may be governed by an erosion-sustained process.

These above inactive ingredients may have multi-functional purposes including the carrying, stabilizing and controlling the release of the antibiotic and/or other therapeutic agent(s). The sustained release process, for example, may be by a solution-diffusion mechanism or it may be governed by an erosion-sustained process.

In some embodiments, a pharmaceutically acceptable formulation comprising a bioactive agent is provided, wherein the formulation is a freeze-dried or lyophilized formulation containing the matrix. Typically, in the freeze-dried or lyophilized formulation an effective amount of a bioactive agent is provided. Lyophilized formulations can be reconstituted into solutions, suspensions, emulsions, or any other suitable form for administration or use. The lyophilized formulation may comprise the liquid used to reconstitute the bioactive agent. Lyophilized formulations are typically first prepared as liquids, then frozen and lyophilized. The total liquid volume before lyophilization can be less, equal to, or more than the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored at or below 30° C., for example, refrigerated at 4° C., or at room temperature (e.g., approximately 25° C.).

Lyophilized formulations of the bioactive agent are typically reconstituted for use by addition of an aqueous solution to dissolve the lyophilized formulation. A wide variety of aqueous solutions can be used to reconstitute a lyophilized formulation. In some embodiments, lyophilized formulations can be reconstituted with a solution containing water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used. In some embodiments, the solutions do not contain any preservatives (e.g., are preservative-free).

Additional Therapeutic Agents

In some embodiments, in addition to the above bioactive agents, the DBM may contain other therapeutic agents which can also be included as bioactive agents.

Any of a variety of medically and/or surgically useful optional substances can be incorporated in, or associated with, the osteoinductive factors either before, during, or after preparation of the osteoinductive composition. Thus, for example when demineralized bone particles are used to form the material, one or more of such substances may be introduced into the demineralized bone particles, for example, by soaking or immersing the bone particles in a solution or dispersion of the desired substance(s).

Medically/surgically useful substances that can be readily combined with the DBM include, for example, calcium phosphate, calcium sulfate, silicon containing ceramic, collagen, collagen derivatives, insoluble collagen derivatives, naturally derived allogenic bone mineral, naturally derived autogenic bone mineral, fully mineralized bone material or mixtures thereof. Other soluble solids and/or liquids dissolved for combination with the DBM include antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin; biocidal/biostatic sugars such as dextroal and/or glucose; amino acids, peptides, vitamins, inorganic elements, co-factors for protein synthesis; hormones; endocrine tissue or tissue fragments; synthesizers; enzymes such as collagenase, peptidases, and/or oxidases; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone powder, autogenous tissues such blood, serum, soft tissue and/or bone marrow; bioadhesives, bone morphogenetic proteins (BMPs), angiogenic factors, transforming growth factor (TGF-beta), insulin-like growth factor (IGF-1); growth hormones such as somatotropin; bone digestors; antitumor agents; immuno-suppressants; permeation enhancers, e.g., fatty acid esters such as laureate, myristate and stearate monoesters of polyethylene glycol, enamine derivatives and/or alpha-keto aldehydes; and, nucleic acids. The amounts of such optionally added substances can vary widely with optimum levels being readily determined in a specific case by routine experimentation.

In one embodiment, a tissue-derived extract or partially demineralized bone may be added to the demineralized bone matrix. The extract may be derived from any suitable tissue, such as bone, bladder, kidney, brain, skin, or connective tissue. Further, the extract may be derived in any suitable manner. The extract may be allogenic, autogenic, xenogenic, or transgenic. In embodiments wherein the extract is bone-derived, the bone may be cortical, cancellous, or cortico-cancellous and may be demineralized, partially demineralized, or mineralized. In some embodiments, the extract may comprise demineralized bone, partially demineralized bone, mineral derived from bone, or collagen derived from bone. In some embodiments, the tissue-derived extract may be a protein extract.

Bone regeneration involves a multitude of cells (e.g. cartilage, fibroblasts, endothelial, etc.) besides osteoblasts. In various embodiments, stem cells from periosteum tissue may be combined with the DBM. Accordingly, the osteoinductive DBM composition may be used to deliver stem cells, which offers the potential to give rise to different types of cells in the bone repair process. In various embodiments, the additive may comprise radiopaque substances, angiogenesis promoting materials, bioactive agents, and osteoinducing agents.

In certain embodiments, the additive is adsorbed to or otherwise associated with the DBM. The additive may be associated with the osteoinductive DBM composition through specific or non-specific interactions, or covalent or noncovalent interactions. Examples of specific interactions include those between a ligand and a receptor, an epitope and an antibody. Examples of nonspecific interactions include hydrophobic interactions, electrostatic interactions, magnetic interactions, dipole interactions, van der Waals interactions, or hydrogen bonding. In certain embodiments, the additive is attached to the osteoinductive DBM composition, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the osteoimplant. In other embodiments at least three additives are attached to the osteoinductive composition. An additive may be provided within the osteoinductive composition in a sustained release format. For example, the additive may be encapsulated within biodegradable nanospheres, or microspheres.

Exemplary therapeutic agents include but are not limited to IL-1 inhibitors, such as Kineret® (anakinra), which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dilhiocarbamate, and other compounds such as, for example, sulfasalazine.

Application of the Bioactive Agent to the DBM Matrix

In some embodiments, a bioactive agent (including one or more antibiotics) may be disposed on or in the interior of the matrix by hand, electro-spraying, ionization spraying or impregnating, vibratory dispersion (including sonication), nozzle spraying, compressed-air-assisted spraying, injecting, brushing and/or pouring. For example, a growth factor such as rhBMP-2 and/or an antibiotic may be disposed on or in the matrix. In some embodiments, the matrix may comprise sterile and/or preservative free material. The DBM can be implanted by hand or machine in procedures such as for example, laparoscopic, arthroscopic, neuroendoscopic, endoscopic, rectoscopic procedures, or the like.

Application of the bioactive agent to the matrix may occur at the time of surgery, or by the manufacturer, or in any other suitable manner. For example, the bioactive agent may be further reconstituted using a syringe and the syringe can be placed into the interior of the matrix via insertion of a needle or cannula (piercing the matrix), and placing it into the interior of the matrix and injecting the bioactive agent so it is evenly distributed throughout the porous interior.

In some embodiments, the bioactive may be applied to the matrix (i.e., DBM) prior to combining the materials and forming it into the final matrix shape. Indeed, the bioactive agent can be blended into the natural or synthetic polymer (i.e., POE) and poured into molds of the final shape of the matrix. Alternatively, the bioactive agent, such as an antibiotic, analgesic or biologic protein, can be incorporated in a suitable liquid carrier, and applied onto and/or into the porous loaded matrix after forming it into the final shape by soaking, imbibing, dripping, injecting, spraying, or the matrix can be molded into the desired shape.

In some embodiments, the lyophilized bioactive agent can be disposed in a vial by the manufacturer and then the surgeon can mix the diluent with the lyophilized bioactive agent. The matrix then can be parenterally administered to the target tissue site. The term "parenteral" as used herein refers to modes of administration which bypass the gastrointestinal tract and include, for example, intramuscular, intraperitoneal, intrasternal, subcutaneous, intra-operatively, intravenously, intrathecally, intradiscally, peridiscally, epidurally, perispinally, intraarticular, or combinations thereof.

The amount of bioactive agent, in some aspects a growth factor, e.g., bone morphogenetic protein may be sufficient to cause bone and/or cartilage growth. In some embodiments, the growth factor is rhBMP-2 and is contained in one or more carriers in an amount of from 0.05 to 2 mg per cubic centimeter of the biodegradable carrier and/or DBM. In some embodiments, the growth factor is rhBMP-2 and is contained in one or more carriers in an amount of from 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95. to 2.0 mg per cubic centimeter of the biodegradable carrier. In some embodiments, the amount of rhBMP-2 morphogenetic protein is from 2.0 to 2.5 mg per cubic centimeter (cc) of the biodegradable carrier. In some embodiments, the amount of rhBMP-2 morphogenetic protein is from 2.0, 2.05, 2.10, 2.15, 2.20, 2.25, 2.30, 2.35, 2.40, 2.45 to 2.50 mg per cubic centimeter (cc) of the biodegradable carrier.

In some embodiments, the bioactive agent is an antibiotic and is contained in one or more carriers in an amount of from 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95. to 2.0 mg per cubic centimeter of the biodegradable carrier. In some embodiments, the amount of antibiotic is from 2.0 to 2.5 mg per cubic centimeter (cc) of the biodegradable carrier. In some embodiments, the amount of rhBMP-2 morphogenetic protein is from 2.0, 2.05, 2.10, 2.15, 2.20, 2.25, 2.30, 2.35, 2.40, 2.45 to 2.50 mg per cubic centimeter (cc) of the biodegradable carrier.

In some embodiments, the bioactive agent is supplied in an aqueous buffered solution. Exemplary aqueous buffered solutions include, but are not limited to, TE, HEPES (2-[4-(2-hydroxyethyl)-1-piperazinyl]ethanesulfonic acid), MES (2-morpholino-ethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In various embodiments, the buffer concentration can be from about 1 mM to 100 mM. In some embodiments, the BMP-2 can be provided in a vehicle (including a buffer) containing sucrose, glycine, L-glutamic acid, sodium chloride, and/or polysorbate 80.

In some embodiments, the DBM may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

Apparatus for and Method of Tissue Processing

Figure 2:
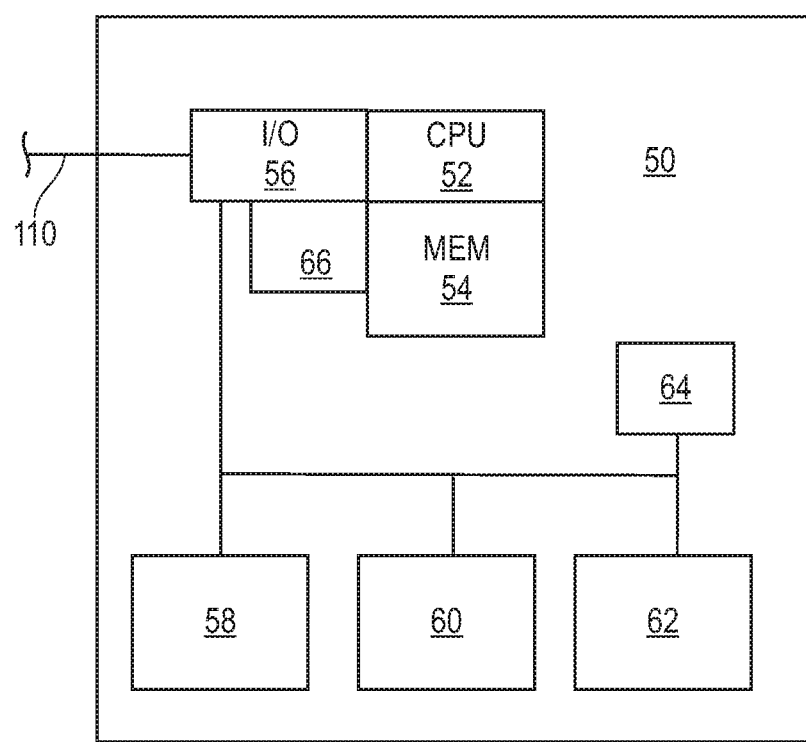
FIG. 2 is a block diagram of an embodiment of a controller according to an aspect of the present application.

Referring to FIG. 1, a block diagram of an embodiment of a first tissue processing apparatus 40 of the present application is shown. A controller 50 is provided for effecting operation of the first tissue processing apparatus 40. For purposes of this disclosure, the controller 50 may be embodied as a general purpose computer, for example, a personal computer, or as an industrial type controller. As further shown in FIG. 2, the controller 50 includes a CPU 52, a memory 54, an Input/Output (I/O) unit 56, a display device 58, an input device 60, and a printing device 62. The display device 58, input device 60, and printing device 62, although shown within the controller 50 block, need not be integral with the controller 50, but may be functionally connected to the CPU 52 and external to a housing enclosing the CPU 52. The display device 58 may be embodied as any type of device capable of visually communicating with an operator of the apparatus 40 such as, without limitation, one or more annunciators, digital displays, flat panel displays, CRTs, or other devices capable of providing visual indications relating functioning of the apparatus 40. The input device 60 may be embodied as buttons, knobs, keypads, touchpads, a computer mouse or trackball, a keyboard, a microphone and voice recognition software and associated hardware, or other input device, either integral with the housing of the controller 40 or external to the housing of the controller. The printing device 62 may be embodied as any device capable of providing a hard copy output. A sound transducer 64 optionally is provided to effect audible communication relating operation of the controller 50. The memory 54 comprises any combination of RAM, ROM, hard drive, flash drive, or CD reader and disc, as required to store instructions to operate the CPU 52 to effect control of the tissue processing apparatus 40. The memory 54 has stored therein instructions in the form of executable programming which is described below with reference to flow charts. Those skilled in the art will appreciate that software executing procedures describe herein may be written in any language which can be compiled to operate the CPU 52.

Returning to FIG. 1, an enclosure 70 is configured to allow opening thereof to accept placement of a tissue sample 72 therein and, subsequent to accepting the tissue sample 72, closure thereof to effect a substantially airtight sealed environment within which the tissue sample 72 is processed. The enclosure 70 is optionally equipped with a fluid level detector 74 arranged to measure a fluid level within the enclosure 70. The enclosure 70 is further optionally equipped with a gas pressure detector 76 arranged to measure a gas pressure in the enclosure. As used herein, gas pressure is intended to include both gas pressure above atmospheric pressure and gas pressure below atmospheric pressure as would result from evacuation of gas from the enclosure 70. The gas pressure detector 76 may include one or more sensors for detection of either a pressurized environment or an evacuated environment.

A draining assembly comprises a drain port 78 communicated with an actuable drain valve 80 controlled by the controller 50. The draining assembly is disposed so as to permit draining of fluid from the enclosure 70 via gravity. Alternatively, another embodiment of the present application has a draining assembly which has an actuable fluid pump communicated with the interior of the enclosure 70 so as to effect draining of fluid from the enclosure 70 in response to the controller 50.

The enclosure 70 includes a gas port 82 communicated to a carbon dioxide sensor unit 84 and a relief valve 86. Further provided is a gas evacuation assembly comprising a gas pumping unit 90 controlled by the controller and communicated to the enclosure to effect removal of gas from the interior of the enclosure 70. Further optionally included are an actuable gas purge valve 88 and the carbon dioxide sensor unit 84 which effect communication of the gas pumping unit to the interior of the enclosure via the gas port 82. The gas purge valve 88 may be omitted if the gas pumping unit 90 maintains a sealed environment in the enclosure 70 when in an inactive state. The carbon dioxide sensor unit 84 may be of a two port feed through sensor type or a one port sensor mated to a tee fitting to provide feed through communication of gas. The gas pumping unit 90 has an exhaust port 92 from which gas evacuated from the enclosure 70 is discharged. Although shown without further connection, it will be understood by those skilled in the art that gases discharged may need to be further held in a suitable container. Further optionally provided is a gas supply unit 94 which is an assembly configured to provide at least one gas to the enclosure 70.

The first tissue processing apparatus 40 further comprises a first reagent supply system 100 (denoted by dashed line enclosure) having a plurality of reagent supply assemblies. A first reagent supply assembly is comprised of a first reagent source unit 100-1, an optionally provided first reagent flow sensor 102-1, and a first reagent supply valve 104-1. Similarly, a second reagent supply assembly is comprised of a second reagent source unit 100-2, an optionally provided second reagent flow sensor 102-2, and a second reagent supply valve 104-2. Likewise, in certain embodiments, a bioactive agent supply assembly is comprised of a bioactive agent source unit 100-ba, an optionally provided bioactive agent flow sensor 102-ba, and a bioactive agent supply valve 104-ba. Further similarly arranged reagent supply assemblies up to an nth reagent supply assembly comprised of an nth reagent source unit 100-n, an optionally provided nth reagent flow sensor 102-n, and an nth reagent supply valve 104-n, are provided wherein n is determined by the number reagents required for a particular processing procedure. It will be understood by those skilled in the art that the position of any one or all of the reagent flow sensors, 102-1, 102-2, 102-ba-102-n, may be interchanged with a corresponding one of the reagent supply valves 104-1, 104-2, 104-ba-104-n. Each of the first through nth reagent supply valves, 104-1, 104-2, 104-ba-104-n, communicates reagent flow into the enclosure 70 via a corresponding one of first through nth reagent supply ports, 106-1, 106-2, 106-ba-106-n.

The controller 50 effects control of the various components of the first tissue processing apparatus 40 via a signal transmission system 110 shown as the interconnection of components of the first tissue processing apparatus 40 to the controller 50. The signal transmission system 110 may take the form of any type of interconnection arrangement suitable to interface the components of the first tissue processing apparatus 40 with the controller 50. For example, the signal transmission system 110 may comprise an IEEE-488 (GPIB), RS-232, RS-485, USB, FireWire or Ethernet interconnection, or any combination thereof as necessitated by interfaces provided on the components of the first tissue processing apparatus 40. Furthermore, the signal transmission system 110 may also comprise individual control lines for driving components of the first tissue processing apparatus 40 that are solenoid or motor actuated such as any of the aforementioned valves 80, 86, 88, and 104-1, 104-2, 104-ba through 104-n. Still further, the signal transmission system 110 may also comprise signal carrying lines for carrying analog signals to and/or from any of the reagent flow sensors 102-1, 102-2, 102-ba through 102-n, the carbon dioxide sensor 84, the fluid level detector 74, or the gas pressure detector 76. The particular type of interconnection used for a given component will be determined by the interface provided on the component. Still further, although the signal transmission system 110 is shown physically interconnecting the controller 50 with the components of the first tissue processing apparatus 40 for purposes of clarity, this physical interconnection is not limiting insofar as the signal transmission system 110 may be effected wirelessly via optical (infrared for example) or RF means. The I/O unit 56 comprises interfaces for the various interfaces used as required by the interconnection used. The controller 50 further includes a timer unit 66 for tracking real time and time intervals. The timer 66, although shown separately, is optionally integrated in the CPU 52.

The reagent source units, 100-1 through 100-n, are each shown optionally (by dash line representation) connected to the signal transmission system 110. In an embodiment of the present application wherein various ones of the reagent source units, 100-1 through 100-n, are arranged to effect gravity feed of a reagent, control of the various ones need not be effected via the signal transmission system. Feeding of the reagent is effected by opening a desired one of the reagent supply valves, 104-1 through 104-n. If any of the reagent source units, 100-1 through 100-n, provide a reagent by means of actively feeding a reagent, such as by a pump or other fluid propelling arrangement, such reagent source units are controlled and connected to the signal transmission system 110 so that the controller 50 can effect control to direct supply of the reagent by the reagent source units 100-1 through 100-n in conjunction with opening a respective one of the reagent supply valves 204-1-204-n.

The reagent flow sensors 102-1, 102-2, 102-ba through 102-n, are optionally provided in the first tissue processing apparatus. In an embodiment including the reagent flow sensors 102-1, 102-2, 102-ba through 102-n, the amount of any reagent supplied to the enclosure 70 is determined by monitoring the respective one of the reagent flow sensors 102-1 through 102-n. However, various ones or all of the reagent flow sensors 102-1 through 102-n are optionally omitted and the amount of reagent supplied is determined by output of the fluid level detector 74. Conversely, the fluid level detector 74 is shown as optionally provided because the amount of reagent supplied may be determined via the reagent flow sensors 102-1, 102-2, 102-ba through 102-n. In some embodiments, the fluid level detector 74 is provided regardless of use of the reagent flow sensors 102-1, 102-2, 102-ba through 102-n.

Figure 3:
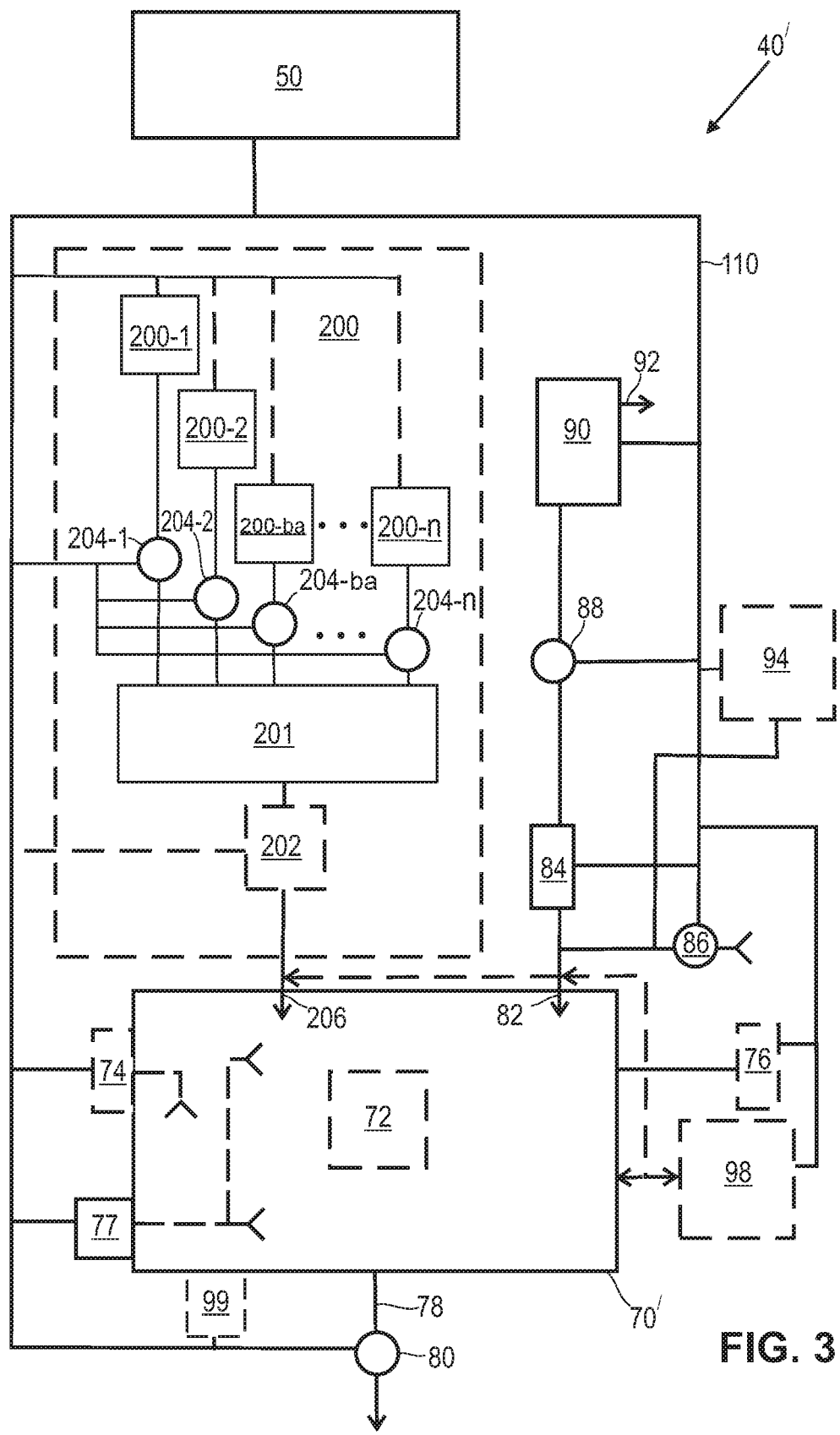
FIG. 3 is a block diagram of another embodiment of a tissue processing apparatus according to an aspect of the present application.

Referring to FIG. 3, a further embodiment of the present application includes a second tissue processing apparatus 40' which is the same as the first tissue processing apparatus 40 except that the first reagent supply system 100 is replaced with a second reagent supply system 200 and the enclosure 70 is replaced by a second enclosure 70'. Components of the second reagent supply system 200 which are the same as components of the first reagent supply system 100 are given like reference designators which are increased by 100, for example, the reagent source units 100-1, 100-2, 100-ba through 100-n are now given the reference designators 200-1, 200-2, 200-ba through 200-n, and likewise the reagent supply valves, 104-1, 104-2, 104-ba through 104-n, are redesignated as 204-1, 204-2, 204-ba through 204-n.

The second reagent supply system 200 differs from the first reagent supply system 100 in that a manifold 201 is now included. Output of the manifold 201 is communicated to flow sensor 202 which, in turn, communicates flow of reagent into the enclosure 70' via a common reagent supply port 206. Hence, the second enclosure 70' is the same as the first enclosure 70 except that the common reagent port 206 replaces the first through nth reagent ports 106-1, 106-2, 106-ba-106-n. As one skilled in the art will appreciate, the second reagent supply assembly 200 requires the one flow sensor 202 instead of a plurality of flow sensors 102-1, 102-2, 102-b-102-n, and the second enclosure 70' thus has the common reagent supply port 206 instead of the plurality of reagent supply ports 106-1, 106-2, 106-ba-106-n. In a further embodiment of the present application a tissue processing apparatus of the present application employs both the first and second reagent supply systems, 100 and 200, in combination with each other wherein some reagent source units will be communicated to the enclosure via a manifold and at least one other reagent source unit is communicated to the enclosure as configured in the first reagent supply assembly 100 without passage through a manifold.

Figure 4:
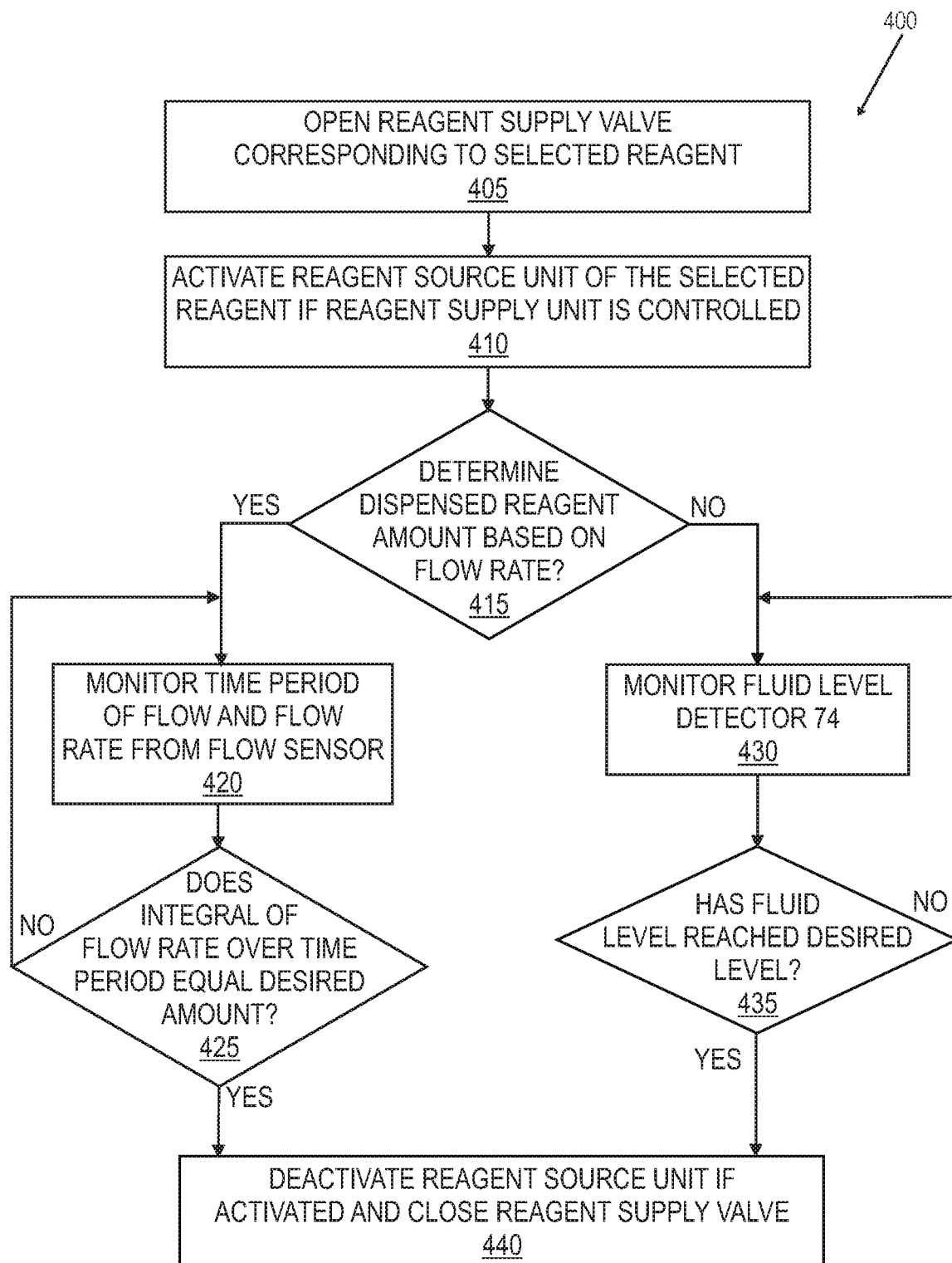
FIG. 4 is a flow chart of an embodiment of an operating procedure for supplying reagent according to an aspect of the present application.

Referring to FIG. 4, a reagent supply procedure 400, to be effected by the controller 50, is shown in a flow chart which may be applied to the first or second tissue processing apparatus 40, (40'). (Reference designators for the second tissue processing apparatus 40' are shown for clarity in parenthesis). The procedure begins with step 405 wherein one of the reagent supply valves 104-1, 104-2, 104-ba-104-n, (204-1-204-n), which corresponds to a selected reagent is opened by the controller 50. In the following step 410, if the selected reagent is supplied from an actuable one of the reagent source units 100-1, 100-2, 100-ba-100-n, (200-1-200-n), the actuable one of the reagent source units 100-1, 100-2, 100-ba-100-n, (200-1-200-n), is activated by the controller 50 to supply the selected reagent. In step 415, it is determined whether the amount of reagent is to be determined using a corresponding one of the reagent flow sensors 102-1, 102-2, 102-ba-102-n, (202). It will be realized by those skilled in the art having the benefit of the present disclosure that step 415 may be omitted if the procedure is to be used employing a known one of flow sensing or level detection to determine an amount of reagent supplied to the enclosure 70 (70'), in which case the flow will proceed from step 410 to the respective one of step 420 or step 430. If it is determined that flow rate is to be used, the flow proceeds to step 520 wherein time is monitored by the controller 50 to determine a time period of how long the selected reagent is supplied and a flow rate of the selected reagent is determined by the controller from querying the corresponding one of the reagent flow sensors 102-1, 102-2, 102-ba-102-n, (202). The flow then proceeds to step 425 wherein the determined flow rate is integrated over the time period by the controller 50 and the resultant amount is compared with a desired amount of reagent. If the resultant amount does not equal or exceed the desired amount, flow returns to step 420 and supply of the selected reagent continues. If the resultant amount does equal or exceed the desired amount, flow proceeds to step 440. Those skilled in the art will appreciate that a certain amount of time delay will be interposed between successive executions of the monitoring of step 420. Although not shown, it is implicit that such a time delay is incorporated into either step 420 or step 425. If the result of step 415 is negative, such as wherein a flow sensor (previously indicated as optional) is not provided for the selected reagent, flow proceeds to step 430 wherein the fluid level detector 74 is monitored. Next in step 435 it is determined whether the fluid level detected has reached or exceeded the desired level. If the determination is negative, flow returns to step 430 and the fluid level detector is again queried. If the determination of step 430 is positive flow proceeds to step 440. Although not shown, it is implicit that a time delay is incorporated into either step 430 or step 435. In step 440, the controller 50 deactivates the actuable one of the reagent source units 100-1, 100-2, 100-ba-100-n (200-1-200-n), if present, and closes the one of the reagent supply valves 104-1, 104-2, 104-ba-104-n (204-1-204-n) opened in step 405.

Figure 5A:
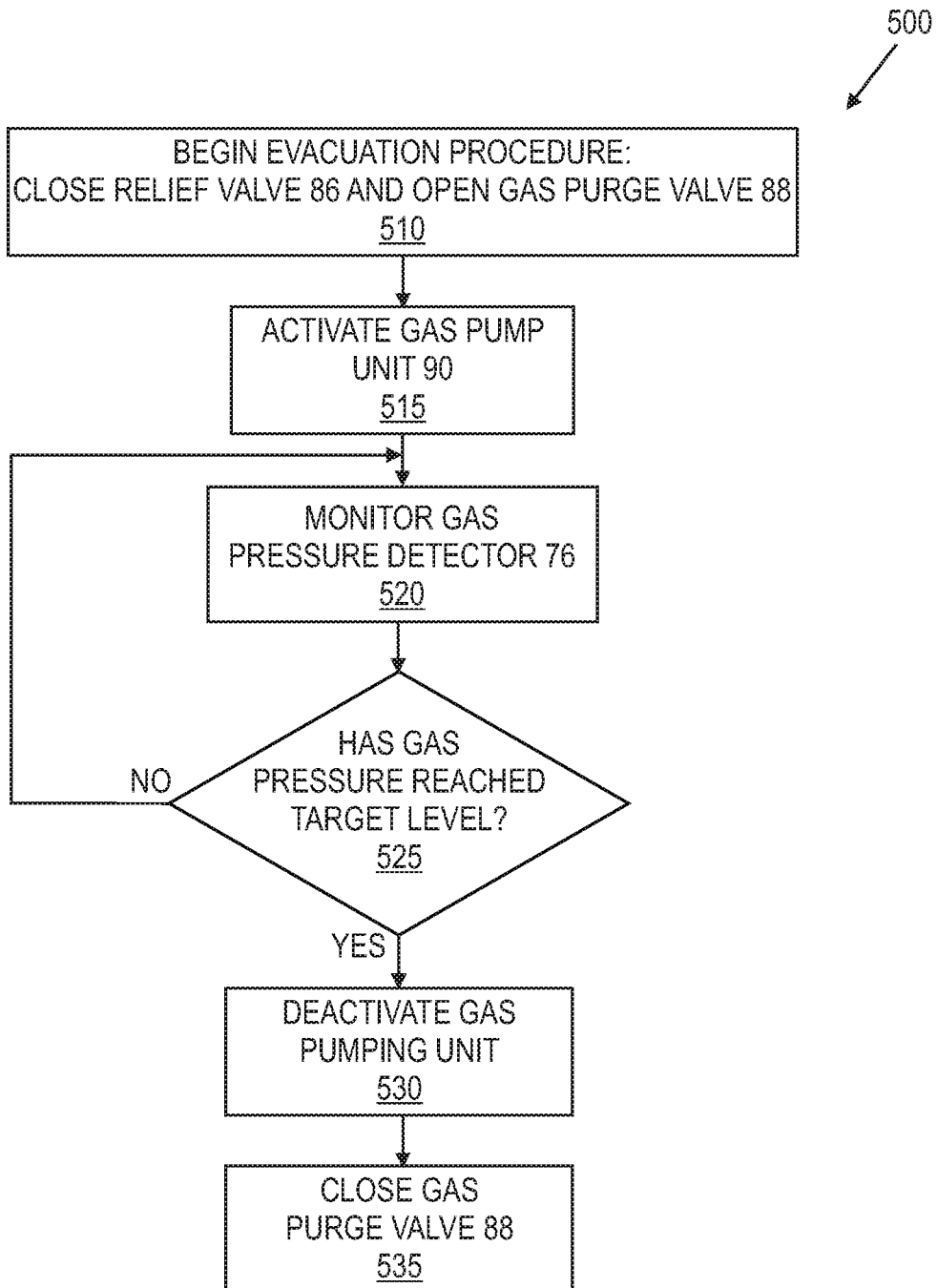
FIG. 5a is a flow chart of an embodiment of an operating procedure for effecting evacuation according to an aspect of the present application.

Referring to FIG. 5a, a flow chart of an evacuation procedure 500, to be effected by the controller 50 of the present application, is shown for use with the first or second tissue processing apparatus 40 and 40' if the optional gas pressure detector 76 is present and to be used. In step 510 the controller 50 closes the relief valve 86 and opens the gas purge valve 88. In step 515, the controller 50 activates the gas pumping unit 90 to draw gas out of the enclosure 70 (70'). Flow proceeds to step 520 wherein the controller 50 monitors the gas pressure detector 76 by querying the gas pressure detector 76 to read a gas pressure in the enclosure 70 (70'). In step 525 a determination is made as to whether the gas pressure read has reached or exceeded a target level. If the determination is in the affirmative, flow then proceeds to step 530. If the determination is in the negative, the flow returns to step 520. As related above with respect to the reagent supply procedure 400, it is implicit that a delay is incorporated into one of step 525 or step 520. In step 530 the controller 50 deactivates the gas pumping unit 90 and then, in step 535, the controller 50 closes the gas purge valve 88.

Figure 5B:
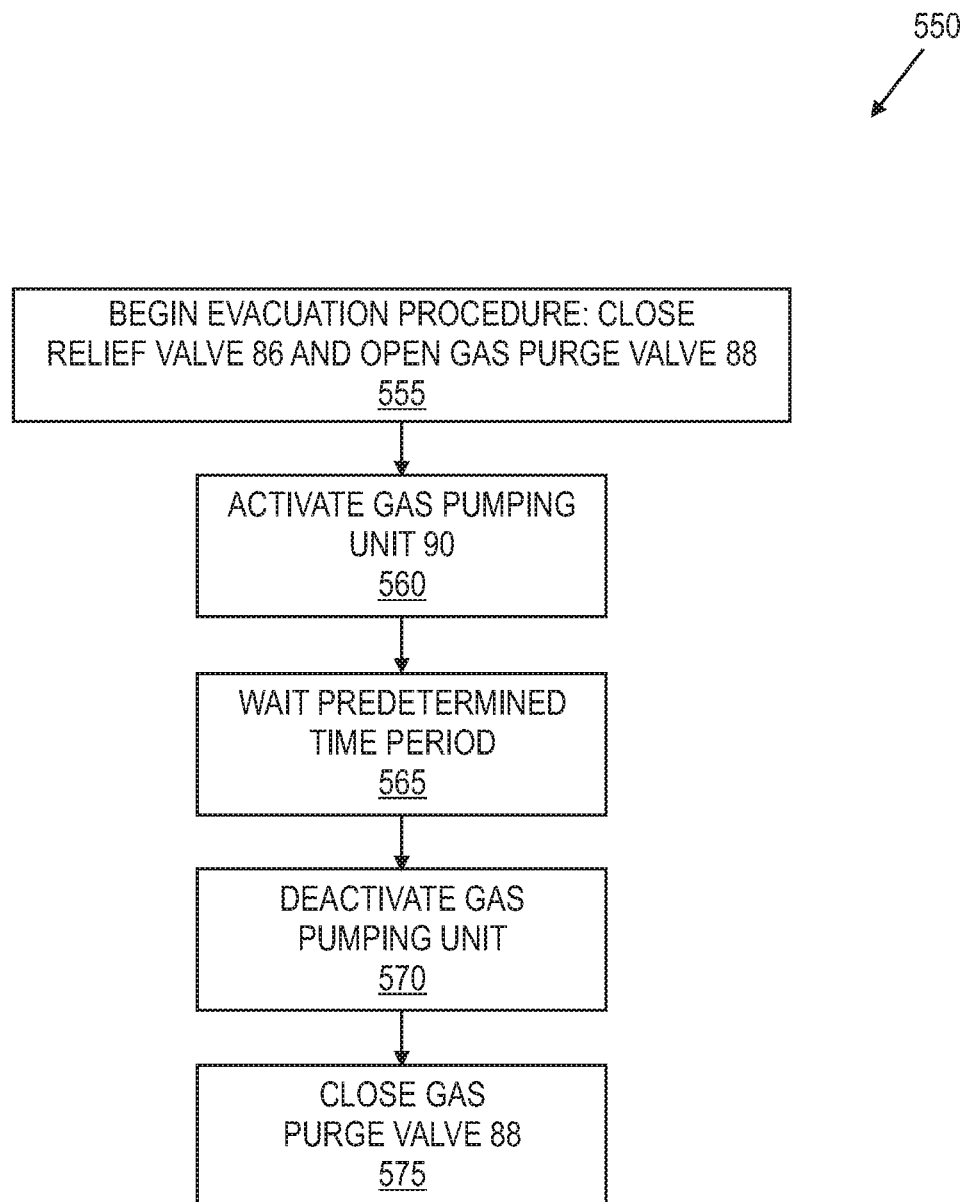
FIG. 5b is a flow chart of another embodiment of an operating procedure for effecting evacuation according to an aspect of the present application.

Referring to FIG. 5b, a flow chart of another evacuation procedure 550, to be effected by the controller 50 of the present application, is shown for use with the first or second tissue processing apparatus 40 and 40' if the optional gas pressure detector 76 is not present, or even if present, it is desired that the gas pressure detector 76 not be employed. In step 555 the controller 50 closes the relief valve 86 and opens the gas purge valve 88. In step 560, the controller 50 activates the gas pumping unit 90 to draw gas out of the enclosure 70 (70'). Flow proceeds to step 565 wherein the controller 50 effects a predetermined delay period. The predetermined delay period may be empirically or otherwise derived as a time sufficient for the gas pumping unit 90 to effect a desired vacuum level in the enclosure 70 (70'). Flow then proceeds to step 570 wherein the controller 50 deactivates the gas pumping unit 90 and then, in step 575, the controller 50 closes the gas purge valve 88. Depending upon the nature of the bioactive agent, the vacuum pressure of enclosure 70 (70') can be varied to a level suitable to ensure the absorption, adsorption or infusion of the bioactive agent into or onto the structure of the DBM matrix.

Referring to FIG. 5c, a flow chart of a vacuum release procedure 580, effected by the controller 50 of the present application, is shown for use with the first or second tissue processing apparatus 40 and 40' if the optional gas pressure detector 76 is present and is to be used. In step 582 the controller 50 opens the relief valve 86. Flow proceeds to step 584 wherein the controller 50 monitors the gas pressure detector 76 by querying the gas pressure detector 76 to read a gas pressure in the enclosure 70 (70'). In step 584 a determination is made as to whether the gas pressure read has reached or exceeded a target level, for example, one atmosphere if the vacuum is to be totally released. If the determination is in the affirmative, flow then proceeds to step 588. If the determination is in the negative, the flow returns to step 584. As related above with respect to the reagent supply procedure 400, it is implicit that a delay is incorporated into one of step 584 or step 586. In step 588 the controller 50 closes the relief valve 86. Depending upon the nature of the bioactive agent, the vacuum pressure of enclosure 70 (70') can be varied to a level suitable to ensure the absortion, adsorption or infusion of the bioactive agent into or onto the structure of the DBM matrix.

Referring to FIG. 5d, a flow chart of another vacuum release procedure 590, to be effected by the controller 50 of the present application, is shown for use with the first or second tissue processing apparatus 40 and 40' if the optional gas pressure detector 76 is not present or is not to be used. In step 592 the controller 50 opens the relief valve 86. Flow proceeds to step 594 wherein the controller 50 effects a predetermined delay period. The predetermined delay period may be empirically or otherwise derived as a time sufficient to effect a desired pressure level in the enclosure 70 (70'). Flow then proceeds to step 596 wherein the controller 50 closes the relief valve 86. Depending upon the nature of the bioactive agent, the vacuum pressure of enclosure 70 (70') can be varied to a level suitable to ensure the absorption, adsorption or infusion of the bioactive agent into or onto the structure of the DBM matrix.

Figure 6A:
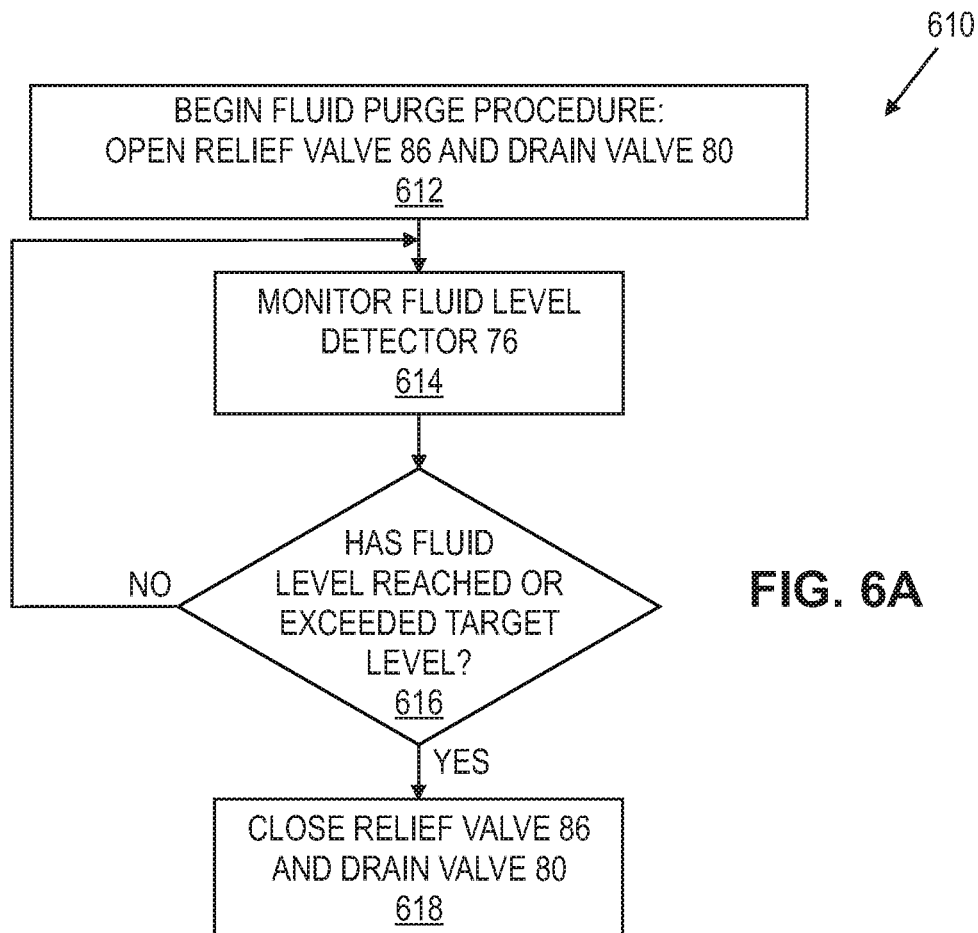
FIG. 6a is a flow chart of an embodiment of an operating procedure for purging as fluid according to an aspect of the present application.

Referring to FIG. 6a, a flow chart of a fluid purge procedure 610, to be effected by the controller 50 of the present application, is shown for use with the first or second tissue processing apparatus 40 and 40' if the optional fluid level detector 74 is present and is to be used. In step 612 the controller 50 opens the relief valve 86 and the drain valve 80. Flow proceeds to step 614 wherein the controller 50 monitors the fluid level detector 74 by querying the fluid level detector 74 to read a fluid level in the enclosure 70 (70'). In step 616 a determination is made as to whether the fluid level read has reached or exceeded a target level, for example, approximately zero if the enclosure 70 (70') is to be totally purged of fluid. If the determination is in the affirmative, flow then proceeds to step 618. If the determination is in the negative, the flow returns to step 614. As related above with respect to the reagent supply procedure 400, it is implicit that a delay is incorporated into one of step 614 or step 616. In step 618 the controller 50 closes the relief valve 86 and the drain valve 80.

Figure 6B:
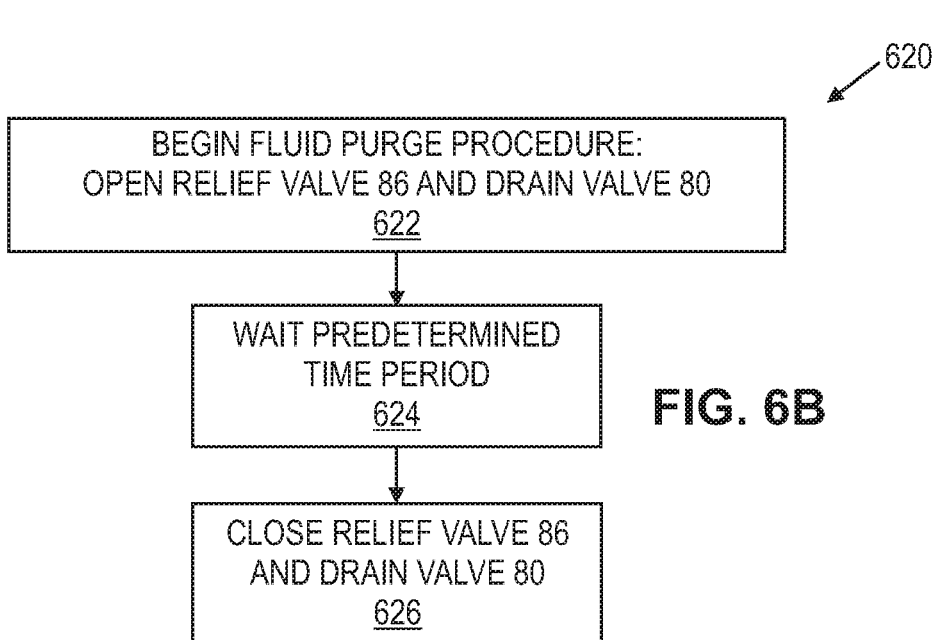
FIG. 6b is a flow chart of another embodiment of an operating procedure for purging as fluid according to an aspect of the present application.

Referring to FIG. 6b, a flow chart of another fluid purge procedure 620, to be effected by the controller 50 of the present application, is shown for use with the first or second tissue processing apparatus 40 and 40' if the optional gas pressure detector 76 is not present or is not to be used. In step 622 the controller 50 opens the relief valve 86 and the drain valve 80. Flow proceeds to step 624 wherein the controller 50 effects a predetermined drain delay period. The predetermined drain delay period may be empirically or otherwise derived as a time sufficient to effect a desired fluid level in the enclosure 70 (70'). Flow then proceeds to step 626 wherein the controller 50 closes the gas relief valve 86 and the drain valve 80.

Figure 7A:
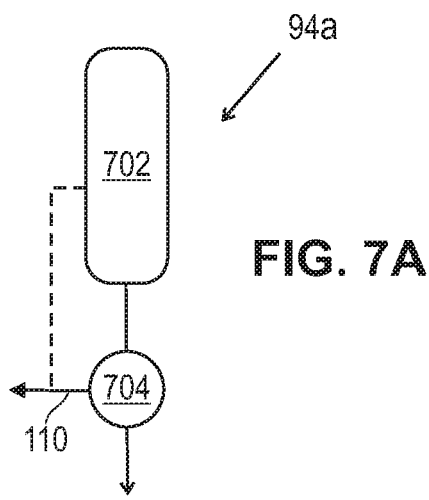
FIG. 7a is a block diagram of an embodiment of a gas supply unit according to an aspect of the present application.
Figure 7B:
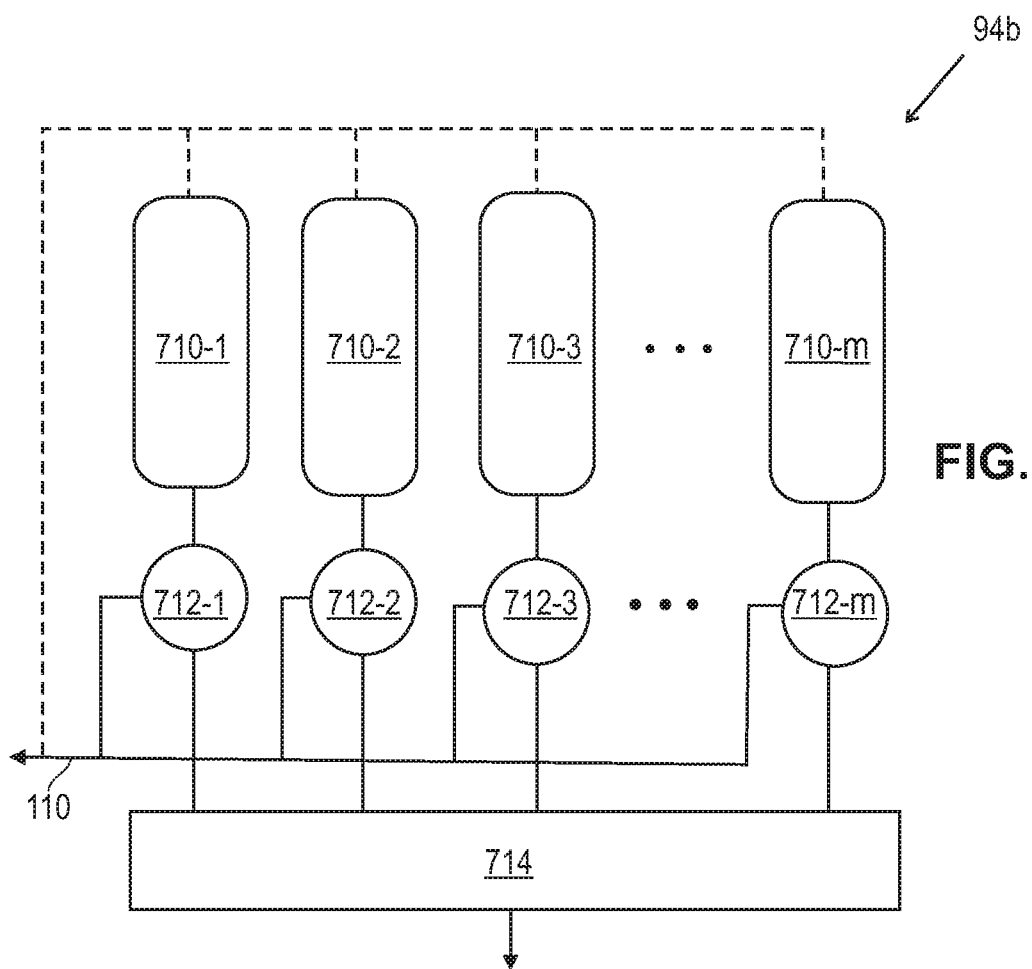
FIG. 7b is a block diagram of another embodiment of a gas supply unit according to an aspect of the present application.

Referring to FIGS. 7a and 7b, embodiments of the gas supply unit 94 of FIGS. 1 and 3 are shown. A first gas supply unit embodiment 94a comprises a gas reservoir 702 and an actuable gas valve 704 which is an arrangement suitable for processing which requires one type of gas. The actuable gas valve 704 communicates gas to the gas port 82 of the enclosure 70 (70'). A second gas supply unit embodiment 94*b* comprises a gas reservoirs **710-1-710-*m* and actuable gas valves 712-1-712-*m*, wherein m corresponds to the number gas supplies required for a given type of processing. The second gas supply unit embodiment 94*b* is an arrangement suitable for processing which requires a plurality of types of gases. The actuable gas valves 712-1-712-*m* communicate gas to a gas manifold 714 which has an output communicated to the gas port 82 of the enclosure 70 (70'). The gas reservoirs 702 and 710-1-710-*m* are commonly tanks of gas, however, the gas reservoirs 702 and 710-1-710-*m* may take any form which can supply gas, liquefied gas, or supercritical gas, such as gas generators or gas sources and pumps which are activated in conjunction with a corresponding one of the valves 704 and 712-1-712-*m*.** In some embodiments of the present application, the bone matrix is treated with supercritical $CO_2$ and liquid $CO_2$ is introduced, for example, by an air pump. The temperature is raised to 105° C. with corresponding pressure about 485 bar. In alternative embodiments, other temperatures and/or pressures above the critical point of $CO_2$ may be used.

Referring back to FIGS. 1 and 3, optionally provided is a thermal assembly 98 which is controlled by the controller 50. The thermal assembly 98 is configured to effect at least one of heating or cooling. The thermal assembly 98 is applied to at least one of reagent feed lines, a gas feed line, or the enclosure 70 to effect either or both of heating and cooling of these elements of the tissue processing apparatus 40 in order to heat or cool contents thereof. In an alternative arrangement the thermal assembly 98 effects either or both of heating and cooling of any of the reagent source units **100-1, 100-2, 100-*ba*-100-*n*, and 200-1, 200-1, 200-*ba*-200-*n*, and the gas reservoirs 702, and 710-1-710-*m*. For purposes of clarity, the thermal assembly 98 is shown as a single block in FIGS. 1 and 3. However, the thermal assembly 98 need not be comprised of a single unit but may be several units dispersed physically in the first or second tissue processing apparatus 40 or 40'**.

A further embodiment of the present application optionally includes a sonication unit 99 under control of the controller 50. The sonication unit is disposed to effect sonication of contents of the enclosure 70 (70") so as to advance reactions therein. For purposes of clarity, the sonication unit 99 is shown as a single block in FIGS. 1 and 3. However, the sonication unit 99 need not be comprised of a single unit but may be several units dispersed physically in the first or second tissue processing apparatus 40 or 40'.

Figure 8:
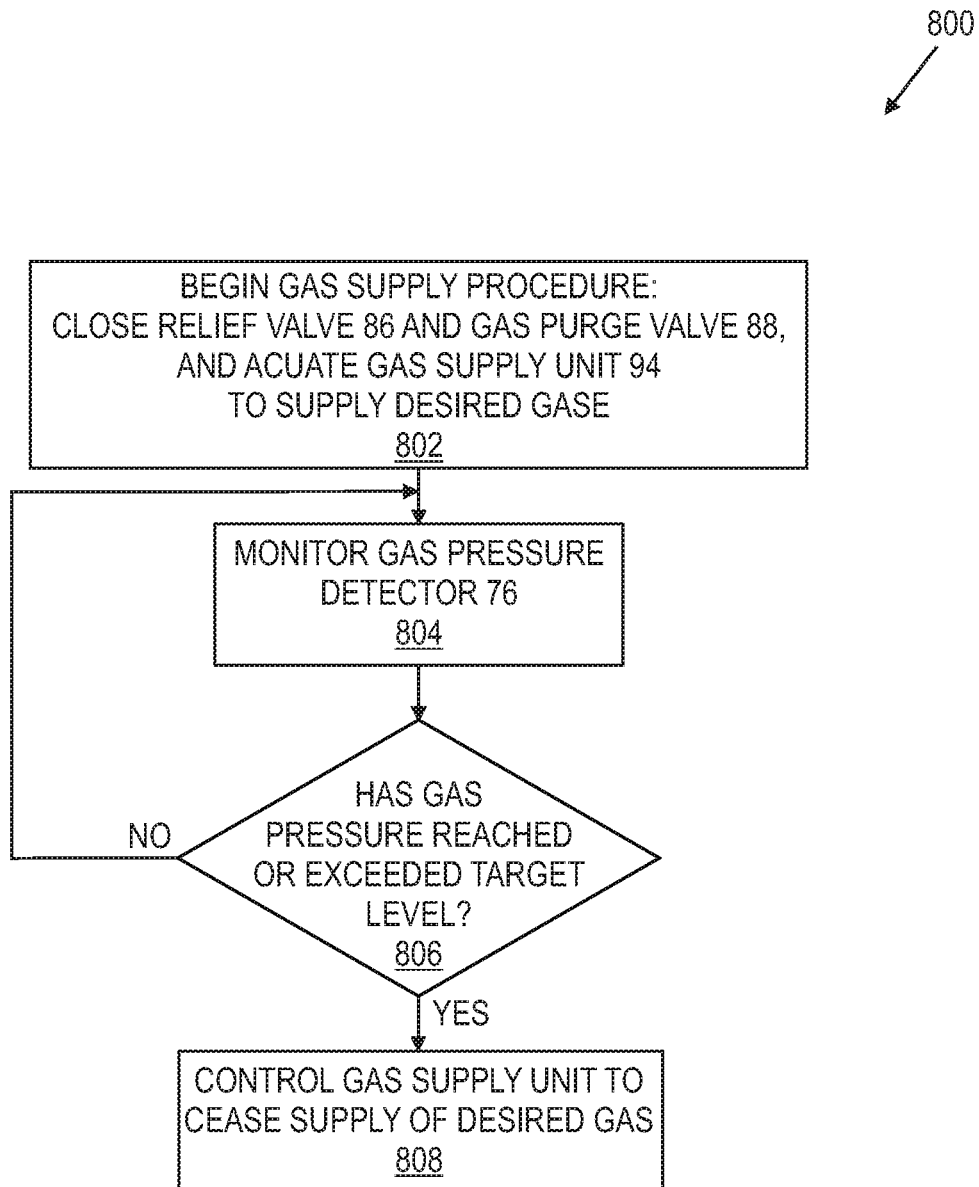
FIG. 8 is a flow chart of an embodiment of an operating procedure for supplying gas according to an aspect of the present application.

Referring to FIG. 8, a flow chart of a gas supply procedure 800, effected by the controller 50 of the present application, is shown for use with the first or second tissue processing apparatus 40 and 40'. In step 802 the controller 50 closes the relief valve 86 and opens the gas purge valve 88, and subsequently actuates the gas supply unit 94 to supply the desired gas. If the first gas supply embodiment **94*a* is present, then the controller 50 actuates the gas valve 704 to open and supply gas from the gas reservoir 702. If the second gas supply embodiment 49*ba* is present, then the controller 50 actuates one of the valves 712-1-712-*m* corresponding to one of the gas reservoirs 710-1-710-*m* containing the desired gas. Flow proceeds to step 804 wherein the controller 50 monitors the gas pressure detector 76 by querying the gas pressure detector 76 to read a gas pressure in the enclosure 70 (70'). In step 806 a determination is made as to whether the gas pressure read has reached or exceeded a target level. If the determination is in the affirmative, flow then proceeds to step 808. If the determination is in the negative, the flow returns to step 804. As related above with respect to other procedures, it is implicit that a delay is incorporated into one of step 804 or step 806. In step 808 the controller 50 controls the gas supply unit 94 to close the valve actuated in step 802** and cease supply of the gas.

The controller 50 accepts instructions to operate the tissue processing apparatus 40 (40') in accordance with requirements of tissue processing procedures which require one or more treatments of tissue with various reagents including, in some embodiments, a bioactive agent, for various time periods, under various atmospheric conditions. Hence, for each reagent there will be an amount, a time period, and an atmospheric condition, and at the end of the time period the reagent will be purged from the enclosure 70 (70'). The amount will usually be an amount necessary to submerge the tissue sample 72 in the reagent and optionally will be a constant amount given that the enclosure 70 (70') is of constant volume and a size of the tissue sample 72 is fairly constant. Hence, although the amount may be varied, it will be realized by one skilled in the art, that the amount for a given one of the tissue treatment apparatus 40 (40') is optionally made constant for each reagent. Of course, if two different reagents are combined in the enclosure 70 (70'), then amounts are set for each reagent. In such a case, combined reagents will have a time period and atmospheric condition associated therewith. If combined reagents are used, they may be serially added to the enclosure 70 (70') or added in parallel. Thus, the processing of the tissue sample 72 is optionally broken down into one or more treatments, with treatment information for each the treatments comprising one or more reagents and corresponding amounts, a time period, and an atmospheric condition. The atmospheric condition is effected by operation of the gas pumping unit 90 to create a low pressure atmosphere, and the gas supply unit 94 to fill the enclosure 70 (70') with a given gas at a given pressure.

Gases are generally supplied in tanks under high pressure. Therefore, such a source would usually be capable of supplying gas to the enclosure 70 (70') to a pressure level required for most treatments. However, it is considered to be within the scope and spirit of the present application to optionally include a gas pump in series with a gas source if the pressure of the gas source by itself is insufficient for a given treatment. Thus, the gas pump would be actuated by the controller 50 to increase the pressure in the enclosure 70 (70') to the required pressure for the treatment.

An embodiment of a method for setting the controller 50 to effect a given procedure for processing of the tissue sample 72 provides for defining one or more treatments for the given processing. Each treatment would then be entered in the controller as a series of commands directing operation of the tissue processing apparatus 40 (40'). An exemplary procedure is one for producing demineralized bone material. In accordance with the procedure the tissue treating apparatus 40 (40') is loaded with reagents for the procedure in the reagent supply system 100 (200). The first reagent source unit 100-1 (200-1) is loaded with an acid, the second reagent source unit 100-2 (200-2) is loaded with sterile water, the third reagent unit 100-3 (200-3) is loaded with alcohol, a fourth reagent source unit 100-4 (200-4) is loaded with glycerol and a fifth reagent source **100-*ba* (200-*ba*)**, in some aspects, is loaded with a bioactive agent.

Figure 9:
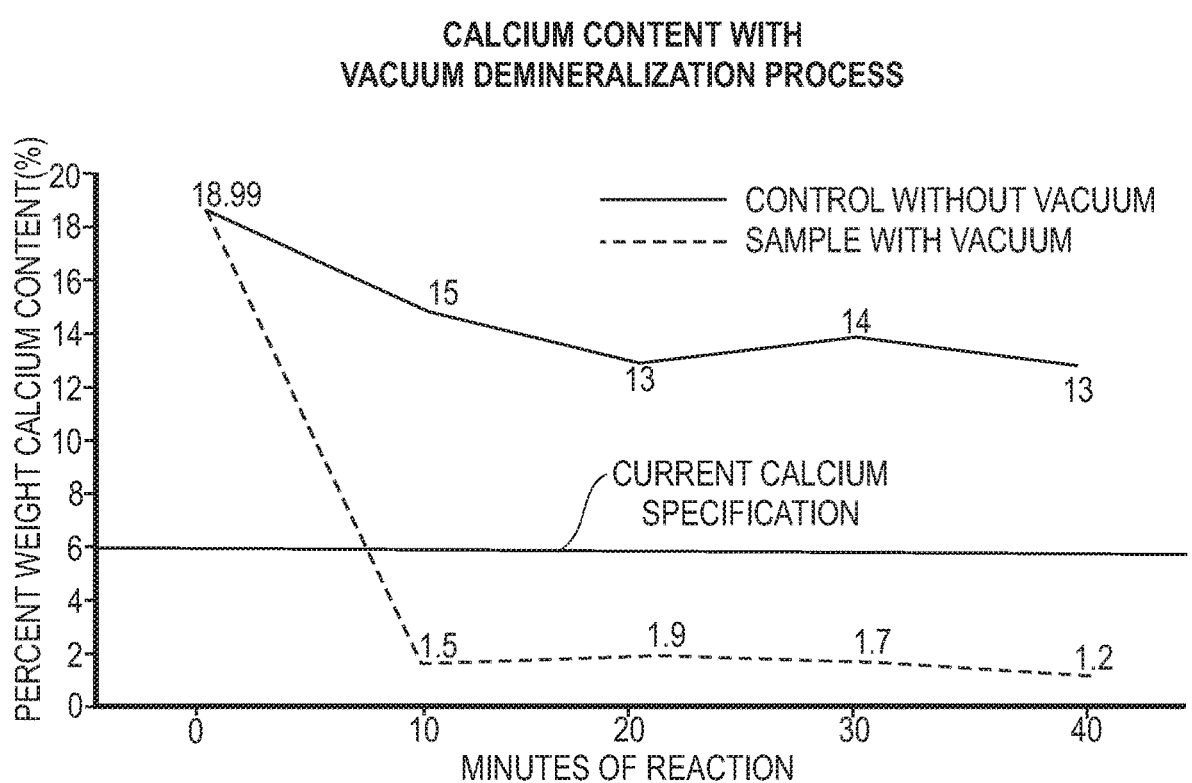
FIG. 9 is a graph depicting calcium content of a bone sample over time showing a first trace of a control sample and a second trace for a sample treated under a low vacuum according to an aspect of the present application.

In order to demineralize bone material faster and more effectively, the bone material is soaked in acid while in a low pressure environment. In this procedure, the bone fibers of the tissue sample are treated with acid under a low vacuum to force equilibrium of the reaction to completion in accordance with Le Chatellier's principle. The removal of carbon dioxide from the system forces the reaction forward to completion. The reaction becomes faster and more complete in comparison with treatment in ambient atmosphere. This effect is shown in FIG. 9 wherein an upper trace illustrates removal of calcium from a control sample which is treated with acid without a vacuum applied while the lower trace illustrates removal of calcium when a low vacuum is applied. As shown, after 10 minutes the control sample treated with acid has the calcium content lowered to 15% while a sample treated with acid in a low vacuum atmosphere has calcium lowered to 1.5%. Therefore, as the automated system allows for controlled removal of reactants (e.g., $CO_2$ via vacuum), the reaction can proceed at a faster rate and reach equilibrium faster so as to enhance processing of the sample, reduce time, and enhance efficiency (e.g., reduce transfer steps) and reduce excessive amounts of reagents to be added to the reaction.

Figure 10:
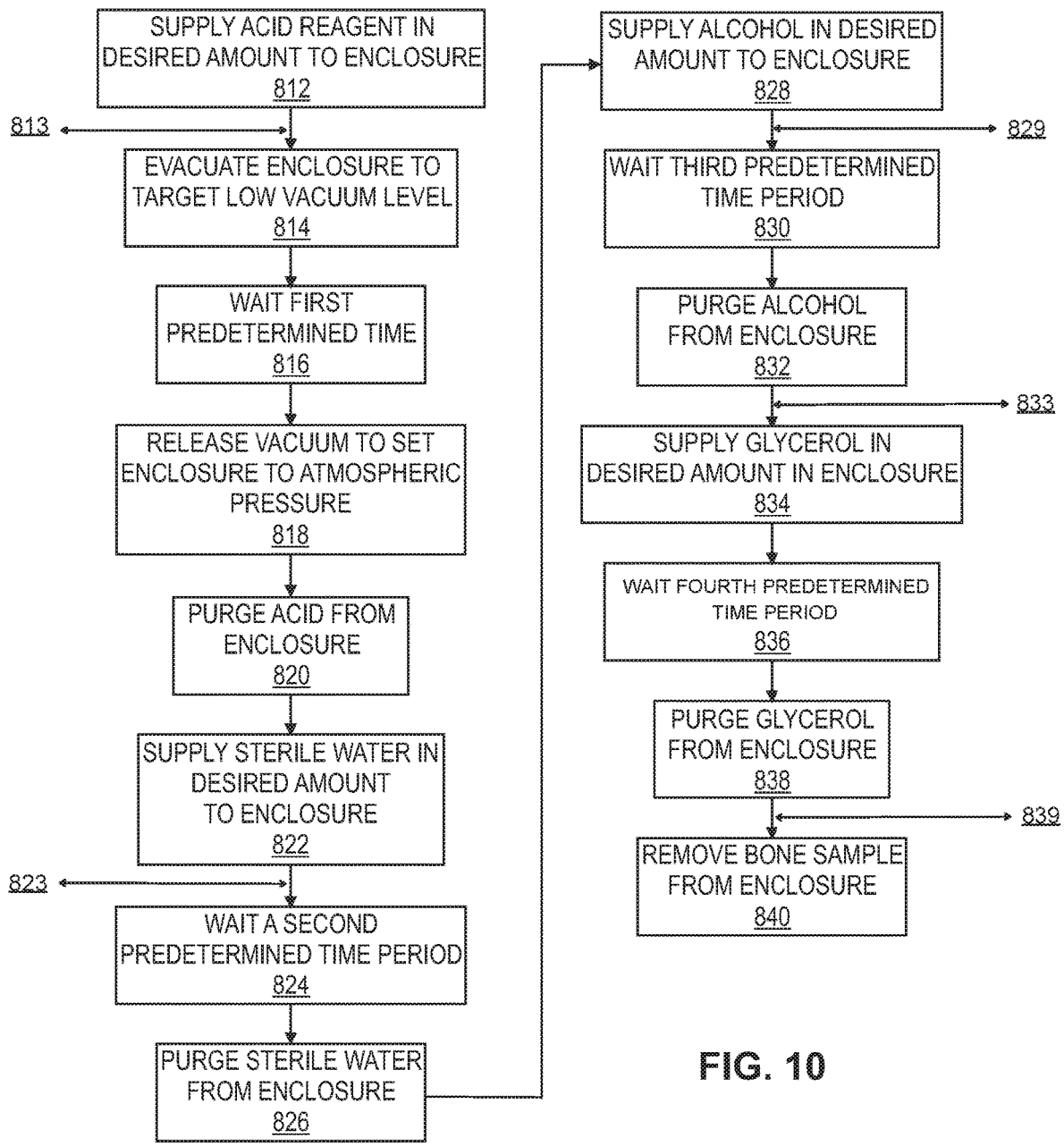
FIG. 10 is a flow chart of an embodiment of a treatment procedure according to an aspect of the present application.

The controller 50 is loaded with instructions to effect a processing procedure comprising a series of operations defined in the foregoing flowcharts of procedures which, for purposes of clarity, are considered sub-procedures to the processing procedure. An exemplary processing procedure implemented by the series of operations of sub-procedures is shown in FIG. 10 and begins in step 812, wherein the controller 50 supplies acid reagent in desired amount to enclosure 70 (70'). In step 814 the controller 50 evacuates the enclosure 70 (70') to a target low vacuum level. The low vacuum removes carbon dioxide from the enclosure 70 (70') to accelerate the removal of calcium from the bone sample 72. In step 816 the controller 50 waits a first predetermined time. In step 818 the controller 50 releases the vacuum to set enclosure 70 (70') to atmospheric pressure. In step 820 the controller 50 purges the acid reagent from the enclosure 70 (70'). In step 822 the controller 50 supplies sterile water in desired amount to the enclosure 70 (70') to effect washing of the bone sample 72. In step 824 the controller 50 waits a second predetermined period of time so that the sterile water has time to remove remaining acid reagent from the bone sample 72. In a next step 826 the controller 50 purges the sterile water from the enclosure 70 (70'). In a following step 828, the controller 50 supplies alcohol in a desired amount to the enclosure 70 (70'). The alcohol delipidizes the bone sample 72 while the controller 50 waits a third predetermined time period in step 830, following which the controller purges the alcohol from the enclosure 70 (70'). Next, in step 834 the controller 50 supplies glycerol in a desired amount to the enclosure 70 (70') to act as a chemical chaperone to osteoinductive proteins in order to reduce, prevent, or reverse denaturation as related previously in this disclosure. Following the controller waiting a fourth predetermined time period, in step 836 the controller 50 purges the glycerol from the enclosure 70 (70') in step 838. Lastly, the operator removes the bone sample from the enclosure 70 (70') in step 840.

The procedure presented in FIG. 10 is not necessarily limited to the order of steps shown. For example, steps 828-832 which delipidize the bone sample 72, may be conducted prior to steps 812-820 which effect the demineralization of the bone sample 72. Also the steps listed are not exclusive to other steps. For example, during the demineralization of the bone sample 72, in the partially evacuated atmosphere, carbon dioxide is produced. In accordance with Le Chatellier's principle, the demineralization reaction is driven forward by a reduction of carbon dioxide effected by the partial evacuation. Thus, a sub-procedure for further evacuation may be added in response to a rise in carbon dioxide level during acid treatment. Such a sub-procedure is discussed below. Another example is addition of further washing conducted by repetition of steps 822-826 elsewhere in the processing procedure. Still another example is that another reagent may be added to the processing procedure for application to the tissue sample 72.

In other embodiments, at least one bioactive agent can be supplied in desired amounts at various stages of the demineralization process. As illustrated in FIG. 10, in some embodiments, a bioactive agent can be supplied at step 813, right after an acid reagent is added to enclosure 70 (70'). In other embodiments, as again illustrated in FIG. 10, a bioactive agent can be supplied at step 823, after sterile water is supplied to enclosure 70 (70'). In some embodiments, the bioactive agent can be supplied at step 829, after alcohol is supplied at step 828 to enclosure 70 (70'). In further embodiments, the bioactive agent can be supplied at steps 833 and 839, that is before glycerol addition to enclosure 70 (70') and after glycerol has been purged from enclosure 79 (70'), respectively.

In various embodiments, depending upon the nature of the bioactive agent, the vacuum pressure of enclosure 70 (70') can be varied to a level suitable to ensure the absortion, adsorption or infusion of the bioactive agent into or onto the structure of the DBM matrix. The release profile of the bioactive agent form the DBM matrix can be influenced and/or regulated by the extent and depth of infusion penetration of the bioactive agent into the DBM matrix. In certain embodiments, factors such as the length of time of infusion and/or soaking, the vacuum strength, the concentration of the solution containing the bioactive agent, and the timing of its addition are all factors that can influence the release profile of the bioactive agent from the DBM matrix.

Figure 11:
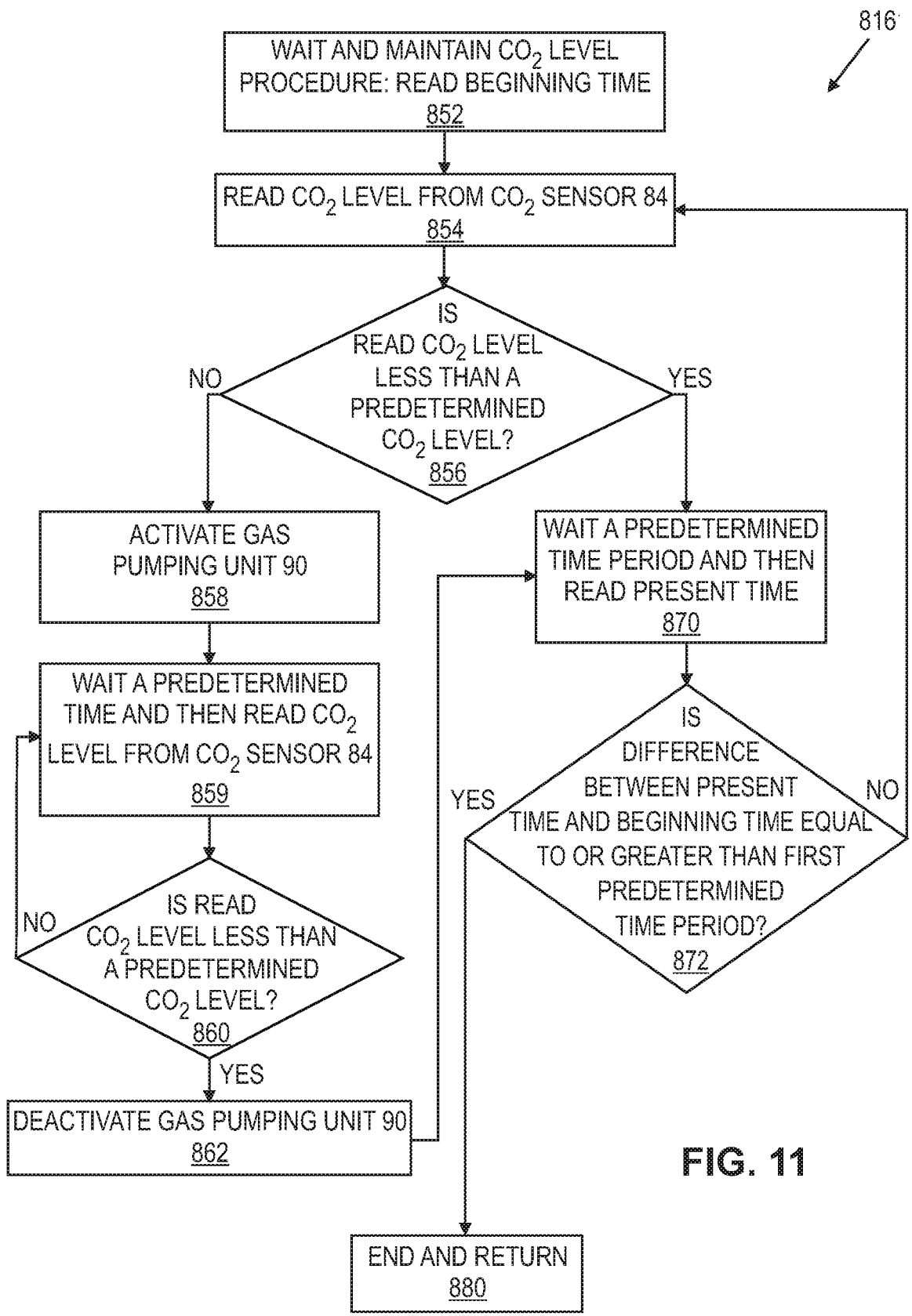
FIG. 11 is a flow chart of an embodiment of an operating procedure according to an aspect of the present application.

A further embodiment of the present application includes monitoring the carbon dioxide level during a modified version of the step 816 and effecting further evacuation of the enclosure 70 (70') in order to keep the carbon dioxide level below a predetermined level. Referring to FIG. 11, a flowchart of a modified step 816 shows implementation of a wait and maintain $CO_2$ level procedure 816'. In step 852 the controller 50 reads a present time for use in later determining whether the first predetermined time period has elapsed. In step 854 the controller 50 reads the $CO_2$ level from the $CO_2$ sensor unit 84 and in step 856 the controller 50 determines whether the read $CO_2$ level is less than the predetermined $CO_2$ level which is the target level. If the determination is negative, flow proceeds to step 858 wherein the controller 50 activates the gas pumping unit 90. Next, in step 859 the controller 50 waits a predetermined time period to permit some evacuation to be accomplished and then reads the $CO_2$ from the $CO_2$ sensor 84. In step 859 the controller 50 determines whether the read $CO_2$ level is less than a predetermined level. If the determination is in the affirmative, flow proceeds to step 862 wherein the controller 50 deactivates the gas pumping unit 90 and flow then proceeds to step 870 discussed below. If the determination is in the negative, the flow proceeds from step 860 back to step 859 for further waiting and a further $CO_2$ reading to be taken. Returning to step 856, if the determination is positive flow proceed to step 870 wherein the controller waits a predetermined time and then reads a present time. Next, in step 872 the controller 50 determines if the difference between the read present time and the read beginning time is equal to or greater than the first predetermined time period originally referenced in step 816 of FIG. 10. If the determination is positive, flow proceeds to step 880 which ends the wait and maintain $CO_2$ level procedure 816'. If the determination is in the negative, the flow returns to step 854. In this manner, the $CO_2$ level procedure 816' directs the controller 50 to maintain the $CO_2$ level at or below the predetermined $CO_2$ level while allowing passage of the first predetermined time period.

Figure 12:
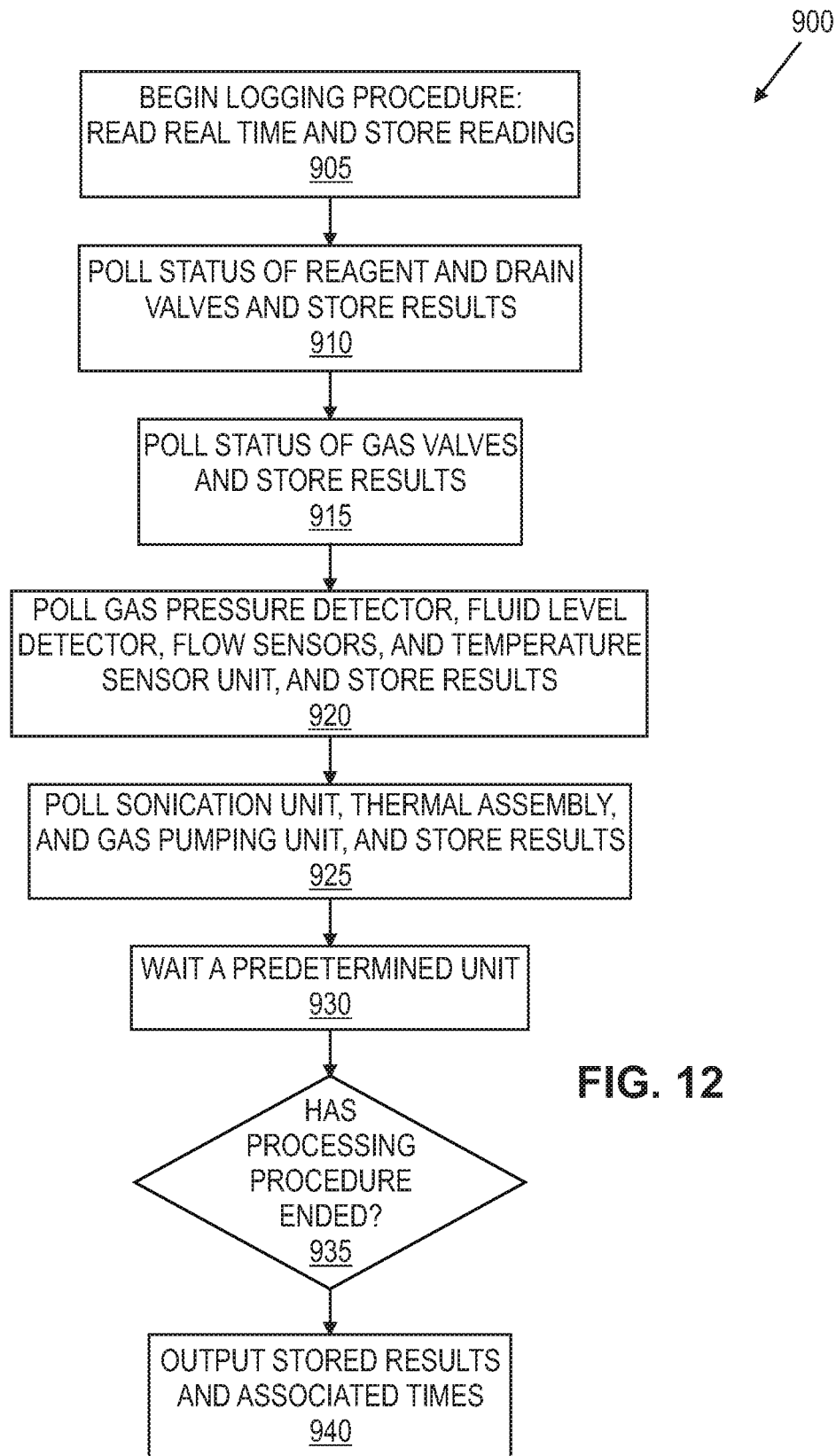
FIG. 12 is a flow chart of an embodiment of a data recording and storage procedure according to an aspect of the present application.

A still further embodiment of the present application comprises a logging procedure 900 shown in FIG. 12. The logging procedure 900 is run in the background of processing procedures, such as the processing procedure shown in FIG. 10, so as to log a status of the components of the tissue processing apparatus 40 (40') and conditions in the enclosure 70 (70'). To this end, a temperature sensor unit 77 is dispose to measure a temperature inside the enclosure 70 (70'). Optionally, the temperature sensor unit 77 has multiple sensors at displaced from each other to measure temperatures at different positions inside the enclosure 70 (70'). This configuration allows measurement of a fluid reagent in a lower portion of the enclosure 70 (70') while also measuring a temperature of an atmosphere above the fluid reagent. Temperature sensors of any type suitable for the environment inside the enclosure 70 (70') may be used, for example and without limitation, thermocouples, thermistors, silicon bandgap temperature sensors, or optical infrared sensors are optionally used. A single type of temperature sensor may be use or combinations of different types of temperature sensors may be used to exploit differing characteristics of the temperature sensors. The logging procedure begins at step 905 in response to the beginning of a processing procedure at which point the controller 50 reads a real time from the timer 66 and stores the real time in the memory 54. In step 910, the controller 50 polls some or all of the reagent supply valves 104-1, 104-2, 104-ba-104-n (200-1-200-n) (and associated ones of the reagent source units 100-1, 100-2, 100-ba-100-n (200-1-200-n) if actively controlled), and the drain valve 80 and stores results in the memory 54. In step 915 the controller 50 polls some or all of the gas valves 704, 712-1-712-m, the gas purge valve 88, and the gas relief valve 86, and stores the results in the memory 54. In the following step 920, the controller 50 polls the gas pressure detector 76 (if present), the fluid level detector 74 (if present), the reagent flow sensors 102-1, 102-2, 102-ba-102-n and 202 (if present), and the temperature sensor unit 77 and stores the results in the memory 54. The controller 50 then polls the sonication unit 99, the thermal assembly 98, and the gas pumping unit and stores the results in the memory 54 in step 925. In step 930 the controller 50 delays a predetermined time period. This time period may be stored prior to the execution of the processing procedure, or may be stored as a default value, with its value select to provide a sufficient number of readings for evaluating the processing procedure. The aforementioned results are stored associated with the real time stored in step 905. In step 935 the controller 50 determines whether the processing procedure has ended. If the determination is negative, the flow returns to step 905. If the determination is positive, the controller 50 proceeds to step 940 wherein the controller outputs the results stored via the display device 58 and/or the printing device 62. As used herein polling is intended to mean either querying an intelligent device as to its status, or reading a status of a register/memory which in turn controls the signal delivered to actuate a given device. Optionally, the controller 50 may omit one or more of the polled devices if irrelevant to or undesired for a processing procedure being implemented. Additionally, one skilled in the art will realize that the order of the steps of polling may be altered. It is also optional to eliminate storing the results and instead directly output the results via the display device 58 or the printing device 62 as they are obtained. However, storing the results allows and outputting the results of successive runs of the processing procedure in a single display or document and effecting differential analysis of the results to evaluate consistency of the processing procedure from one run to the next. This allows identification of undesired and/or desired variations. Further, the controller 50 is optionally programed to actuate an alarm via one or more of the sound transducer 64, the display device 58, or the printing device 62, if a measured result is outside a programmed range. Thus, quality control is enhanced and errors in recording processing procedure variables are eliminated or reduced.

One of the numerous problems this present disclosure application solves is the difficult and onerous data collection and documentation process required by the manual system. The controller and the software provided eliminates or reduces this problem as the monitored values, times, pressure, temperature, are able to be uploaded and stored to a database. This provides a complete audit trail which can be used for quality assurance and process optimization.

A feature of the present application optionally comprises any number of the reagent supply valves 104-1, 104-2, 104-ba-104-n (200-1-200-n) being actuable such that individual ones of the reagent supply valves 104-1, 104-2, 104-ba-104-n (200-1-200-n) are settable to be opened in varying degrees. Such valves are also optionally controllable in conjunction with associated ones of the reagent flow sensors 102-1, 102-2, 102-ba-102-n and 202 (if present) in a feedback arrangement wherein the controller 50 monitors flow and adjusts corresponding valves accordingly to achieve a target reagent flow value. Alternatively, if varied control is not required, the reagent supply valves 104-1, 104-2, 104-ba-104-n (200-1-200-n) are actuable to be either opened or closed. Similarly, some or all of the gas valves 704, 712-1-712-m, the gas purge valve 88, and the gas relief valve 86, are optionally settable to be opened in varying degrees. Such valves are also optionally controllable in conjunction with associated ones of the pressure sensor 76 in a feedback arrangement wherein the controller 50 monitors a rate of pressure change and adjusts corresponding valves accordingly to achieve a target gas flow value. Alternatively, if varied control is not required, the gas valves 704, 712-1-712-m, the gas purge valve 88, and the gas relief valve 86, are actuable to be either opened or closed.

It will be understood by those skilled in the art that the block diagrams of the present disclosure are intended to illustrate functional interconnection of components and do not illustrate relative physical arrangement or orientation except as specifically stated herein. Furthermore, dashed line representations indicate components that are optionally provided but it is further within the spirit and scope of the present application that components that are not shown in dashed line representations may be omitted if unnecessary to a particular processing procedure.

Having described various embodiments of the application with reference to the accompanying drawings, it is to be understood that the application is not limited to those precise embodiments, and that various changes and modifications may be effected therein by one skilled in the art without departing from the scope or spirit of the application as defined in the appended claims. Such modifications include substitution of components for components specifically identified herein, wherein the substitute components provide functional results which permit the overall functional operation of the present application to be maintained. Such substitutions are intended to encompass presently known components and components yet to be developed which are accepted as replacements for components identified herein and which produce result compatible with operation of the present application.

What is claimed is:

1. An apparatus for processing a bone tissue sample, the apparatus comprising:
    a controller;
    an enclosure defining a reaction chamber for accepting the bone tissue sample;
    a reagent supply system configured to receive at least one reagent, the at least one reagent comprising at least one bioactive agent configured to contact the bone tissue sample, and to dispense the at least one reagent into the reaction chamber in response to the controller, the reagent supply system comprising a bioactive agent supply assembly, the bioactive agent supply assembly comprising a bioactive agent flow sensor, a bioactive agent supply valve, and a bioactive agent source unit that provides the at least one bioactive agent into the reaction chamber;
    a gas evacuation assembly communicated to the reaction chamber and configured to pump gas from the reaction chamber in response to the controller;
    a draining assembly communicated to the reaction chamber and configured to drain fluid and the at least one bioactive agent from the reaction chamber in response to the controller; and
    a signal transmission system functionally interconnecting the controller with the reagent supply system, the gas evacuation assembly, and the draining assembly, wherein the at least one bioactive agent comprises a growth factor, a bone morphogenetic protein, an analgesic, an anti-inflammatory, and antibiotic, a cytokine, a chemotherapeutic or a mixture thereof.

2. An apparatus of claim 1, further comprising a fluid level detector disposed to detect a fluid level in the reaction chamber and communicate the fluid level to the controller via the signal transmission system and the bone tissue sample comprises soft tissue.

3. An apparatus of claim 1, further comprising a gas pressure detector disposed to detect a gas pressure in the reaction chamber and communicate the gas pressure to the controller via the signal transmission system and the bone tissue sample is demineralized with the reagent that comprises an acid in the reaction chamber.

4. An apparatus of claim 1, further comprising a carbon dioxide sensor communicated to the reaction chamber to detect a carbon dioxide level in the reaction chamber and communicate the carbon dioxide level to the controller via the signal transmission system and the bone tissue sample is demineralized with the reagent that comprises an acid in the reaction chamber and the porosity of the demineralized bone tissue is controlled.

5. An apparatus of claim 1, further comprising a gas supply unit communicated to the reaction chamber and configured to receive at least one gas and dispense the at least one gas into the reaction chamber in response to the controller, the gas supply unit being functionally interconnected with the controller via the signal transmission system and the bone tissue that is demineralized by controlled soaking with the reagent that comprises an acid in the reaction chamber.

* * * * *